United States Patent
Agley et al.

(10) Patent No.: US 12,378,341 B2
(45) Date of Patent: Aug. 5, 2025

(54) TUNEABLE CELL SUBSTRATES

(71) Applicant: Cambridge Enterprise Limited, Cambridgeshire (GB)

(72) Inventors: Chibeza Chintu Agley, Cambridgeshire (GB); Kevin Chalut, Cambridgeshire (GB); Jose Carlos Rebelo da Silva, Cambridgeshire (GB)

(73) Assignee: Cambridge Enterprise Limited, Cambridgeshire (GB)

( * ) Notice: Subject to any disclaimer, the term of this patent is extended or adjusted under 35 U.S.C. 154(b) by 1003 days.

(21) Appl. No.: 16/772,584

(22) PCT Filed: Dec. 14, 2018

(86) PCT No.: PCT/EP2018/085079
§ 371 (c)(1),
(2) Date: Jun. 12, 2020

(87) PCT Pub. No.: WO2019/115814
PCT Pub. Date: Jun. 20, 2019

(65) Prior Publication Data
US 2020/0399410 A1     Dec. 24, 2020

(30) Foreign Application Priority Data

Dec. 15, 2017 (GB) .................... 1721046

(51) Int. Cl.
| | | |
|---|---|---|
| C08F 220/56 | (2006.01) | |
| B82Y 5/00 | (2011.01) | |
| C08F 222/38 | (2006.01) | |
| C12M 3/02 | (2006.01) | |
| C12N 5/00 | (2006.01) | |
| C12N 5/074 | (2010.01) | |
| C12N 5/077 | (2010.01) | |

(52) U.S. Cl.
CPC ........ *C08F 220/56* (2013.01); *C08F 222/385* (2013.01); *C12M 3/02* (2013.01); *C12N 5/0068* (2013.01); *C12N 5/0607* (2013.01); *C12N 5/0654* (2013.01); *B82Y 5/00* (2013.01); *C12N 2501/155* (2013.01); *C12N 2506/45* (2013.01); *C12N 2533/30* (2013.01)

(58) Field of Classification Search
CPC ..... C08F 220/56; C08F 222/385; C12M 3/02; C12N 5/0068; C12N 5/0607; C12N 5/0654; C12N 2501/155; C12N 2506/45; C12N 2533/30; B82Y 5/00
See application file for complete search history.

(56) References Cited

U.S. PATENT DOCUMENTS

2014/0243428 A1 * 8/2014 Varghese ............... A61K 47/32
524/813

FOREIGN PATENT DOCUMENTS

| EP | 2666486 A1 | 11/2013 |
|---|---|---|
| WO | 2003093785 A2 | 11/2003 |
| WO | 2009026380 A1 | 2/2009 |
| WO | 2010011407 A2 | 1/2010 |
| WO | 2018067789 A1 | 4/2018 |

OTHER PUBLICATIONS

Wen, "Roles of Matrix Ligand Tethering and Density in Stem Cell Differentiation and Migration A Dissertation Submitted in Partial Satisfaction of the Requirements for the Degree of Doctor of Philosophy in Bioengineering", ProQuest LLC, UMI No. 3709295, 2015, pp. 1-131.*
Naomi et al., "Current Insights Into Collagen Type I", Polymers, 2021, 13, 2642, https://doi.org/10.3390/polym13162642, pp. 1-19.*
Pelham, Jr. et al., "Cell Locomotion and Focal Adhesions are Regulated by Substrate Flexibility", Proc. Natl. Acad. Sci. USA, vol. 94, Dec. 1997, pp. 13661-13665.*
Park, et al., "The Effect of Matrix Stiffness on the Differentiation of Mesenchymal Stem Cells in Response to TGF-β", Biomaterials, Elsevier Science Publishers BV, vol. 32, No. 16, pp. 3921-3930, Feb. 10, 2011.
International Search Report in PCT International Application No. PCT/EP2018/085079 mailed Mar. 29, 2019.
Boroviak et al., "Lineage-Specific Profiling Delineates the Emergence and Progression of Naive Pluripotency in Mammalian Embryogenesis," Developmental Cell, Nov. 9, 2015, vol. 35, pp. 366-382.
Caiazzo et al., "Defined three-dimensional microenvironments boost induction of pluripotency," Nature Materials, Mar. 2016, vol. 15, pp. 344-352.
Connelly et al., "Actin and serum response factor transduce physical cues from the microenvironment to regulate epidermal stem cell fate decisions," Nature Cell Biology, Jul. 2010, vol. 12, No. 7, pp. 711-718 and supplementary information.
Dos Santos et al., "MBD3/NuRD Facilitates Induction of Pluripotency in a Context-Dependent Manner," Cell Stem Cell, Jul. 3, 2014, vol. 15, pp. 102-110.

(Continued)

*Primary Examiner* — Patrick D Niland
(74) *Attorney, Agent, or Firm* — Bochner PLLC; Beverly W. Lubit

(57) ABSTRACT

This invention relates to a substrate for mammalian cell culture comprising a co-polymer hydrogel comprising monomeric units of acrylamide, bisacrylamide and a coupling compound, such as 6-acylamidohexanoic acid (6AHA). A cell adhesion molecule, such as a component of the extracellular matrix (ECM), is covalently coupled to the coupling compound monomeric units of the co-polymer. The stiffness and cell adhesion molecule density of the substrate can be independently controlled by altering the concentration of acrylamide and coupling compound in the hydrogel, respectively. Substrates and methods and kits for their production are provided, along with cell culture systems and methods of culturing mammalian cells.

18 Claims, 21 Drawing Sheets

(56) References Cited

OTHER PUBLICATIONS

Engler et al., "Matrix Elasticity Directs Stem Cell Lineage Specification," Cell, Aug. 25, 2006, vol. 126, pp. 677-689.
Geiger et al., "Environmental sensing through focal adhesions," Nature Reviews Molecular Cell Biology, Jan. 2009, vol. 10, pp. 21-33.
Gerecht et al., "Hyaluronic acid hydrogel for controlled self-renewal and differentiation of human embryonic stem cells," Proceedings of the National Academy of Sciences, Jul. 3, 2007, vol. 104, No. 27, pp. 11298-11303.
Guilak et al., "Control of Stem Cell Fate by Physical Interactions with the Extracellular Matrix," Cell Stem Cell, Jul. 2, 2009, vol. 5, pp. 17-26.
Huebsch et al., "Harnessing traction-mediated manipulation of the cell/matrix interface to control stem-cell fate," Nature Materials, Jun. 2010, vol. 9, pp. 518-526.
Meilhac et al., "Active cell movements coupled to positional induction are involved in lineage segregation in the mouse blastocyst," Developmental Biology, 2009, vol. 331, pp. 210-221.
Nichols et al., "Naive and Primed Pluripotent States," Cell Stem Cell, Jun. 5, 2009, vol. 4, pp. 487-492.
Nichols et al., "Suppression of Erk signalling promotes ground state pluripotency in the mouse embryo," Development, 2009, vol. 136, No. 19, pp. 3215-3222.
Ruoslahti, Erkki, "RGD and other recognition sequences for integrins," Annual Review of Cell and Developmental Biology, 1996, vol. 12, pp. 697-715.
Strange et al., "Separating poroviscoelastic deformation mechanisms in hydrogels," Applied Physics Letters, 2013, vol. 102, 031913, pp. 1-4.
Trappmann et al., "Extracellular-matrix tethering regulates stem-cell fate," Nature Materials, Jul. 2012, vol. 11, pp. 642-649.
Versaevel et al., "Spatial coordination between cell and nuclear shape within micropatterned endothelial cells," Nature Communications, 2012, vol. 3, Article No. 671, pp. 1-11.
Wang et al., "Mechanotransduction at a distance: mechanically coupling the extracellular matrix with the nucleus," Nature Reviews Molecular Cell Biology, Jan. 2009, vol. 10, pp. 75-82.
European Chemicals Agency, "Guidance for monomers and polymers," Feb. 2023, Version 3.0, pp. 1-26.
Third Party Observation dated Jan. 23, 2024 in corresponding European Patent Application No. 18826268.7 (4 pages).
Tse et al., "Preparation of Hydrogel Substrates with Tunable Mechanical Properties," Current Protocols in Cell Biology, Jun. 2010, Suppl. 47, pp. 10.16.1-10.16.16.
Examination Report dated Nov. 27, 2023 in corresponding European Patent Application No. 18826268.7 (7 pages).

* cited by examiner

TUNEABLE CELL SUBSTRATES

CROSS REFERENCE TO RELATED APPLICATIONS

This application is a U.S. National Phase application under 35 U.S.C. 371 of International Application No. PCT/EP2018/085079, filed Dec. 14, 2018, which claims priority to and the benefit of GB Application No. 1721046.9 filed Dec. 15, 2017, the entire disclosure of each of which is incorporated herein by reference.

FIELD

The present invention relates to substrates for the culture of mammalian cells, such as stem and progenitor cells.

BACKGROUND

The stem cell field has largely overlooked the influence of mechanical cues on stem cell function, despite the stem cell niche being a highly dynamic mechanical environment. For example, during implantation, the mammalian epiblast (the pluripotent compartment of the embryo) epithelializes, progressing from a tight aggregate to a spread, polarized epithelium. Indeed, during all stages of development and lineage specification, cells perceive and respond to extrinsic physical forces [1], which is referred to as mechanosensing and mechanotransduction [2]. In general, mechanosensing consists of cells actively feeling the stiffness of the extra-cellular matrix (ECM) on which they reside via focal adhesions, then respond by modulating their contractile activity to alter the force balance [3]. The cells' mechanosensing machinery integrates this alteration in intracellular forces with biochemical signalling; and transcriptional activity, morphology and behaviour are altered accordingly [2]. Therefore, mechanical signalling is an essential aspect of cell function because ECM composition varies widely, and tissue stiffness varies from reported values of ~300 Pa for brain and ~100 kPa for bone. These tissue features have been demonstrated to have a strong impact on stem cell differentiation independent of diffusible chemicals [4, 5]. Nonetheless, there is very little current mechanistic understanding of the role that mechanosensing and mechanotransduction play in regulating lineage specification and self-renewal in stem cell niches.

In order to better use mechanical signals to harness stem cell function, there is considerable interest in using biomimetic matrices with tuneable mechanical properties, most commonly using hydrogel substrates, to optimise the cellular microenvironment. Synthetic matrices have been synthesized with different types of hydrogel, including polyacrylamide (PAA) [5], hydroxyl-PAA [6], alginate [7], hyaluronic acid [8] and polyethylene glycol [9]. Most hydrogels are inert and do not allow attachment; however, via specific cross-linking chemistries, ECM can be added. Hydrogel substrates have been extensively used to tune ECM stiffness in order to regulate stem cell fate ([5, 10], reviewed in [11]) and also for cellular reprogramming [9]. A conventional wisdom materialised that, aside from chemical signalling, stiffness was the parameter most responsible for steering stem cell fate; however, lately the distribution and concentration of bioactive materials on the hydrogel surface has emerged as a very important aspect of hydrogel substrate technology and its control over stem cell fate [12]. However, no definitive protocol has been reported that has allowed independent control over ECM stiffness and ligand density, which would empower the broad use of hydrogels in stem cell biology and regenerative medicine.

SUMMARY

The present inventors have developed a cell culture substrate in which both stiffness and amount of cell adhesion can be independently controlled via the alteration of molecular anchoring sites. This may be useful for example in developing optimal conditions for culturing mammalian stem and progenitor cells.

A first aspect of the invention provides a substrate for mammalian cell culture comprising;
  (i) a co-polymer hydrogel comprising monomeric units of acrylamide, bisacrylamide and a coupling compound, and
  (ii) a cell adhesion molecule, said cell adhesion molecule being covalently coupled to the coupling compound monomeric units of the co-polymer.

A second aspect of the invention provides a mammalian cell culture system comprising;
  (a) a substrate comprising
    (i) a co-polymer hydrogel comprising monomeric units of acrylamide, bisacrylamide and coupling compound, and
    (ii) a cell adhesion molecule covalently coupled to the coupling compound monomeric units of the co-polymer;
  (b) a cell culture medium, and optionally
  (c) mammalian cells A third aspect of the invention provides a method of culturing mammalian cells comprising;
  providing a substrate comprising;
    (i) a co-polymer hydrogel comprising monomeric units of acrylamide, bisacrylamide and coupling compound, and
    (ii) a cell adhesion molecule covalently coupled to the coupling compound monomeric units of the co-polymer;
  immersing the substrate in cell culture medium;
  seeding the substrate with mammalian cells; and
  culturing the mammalian cells on the hydrogel.

A fourth aspect of the invention provides a method of producing a cell culture substrate comprising
  producing a solution of monomeric units of acrylamide, bisacrylamide and coupling compound,
  polymerising said monomers to form co-polymer hydrogel comprising acrylamide and coupling compound monomeric units; and
  covalently coupling a cell adhesion molecule to the coupling compound monomeric units to produce the cell culture substrate.

A fifth aspect of the invention provides a kit comprising a substrate of the first aspect.

A sixth aspect of the invention provides a kit comprising;
  a co-polymer comprising monomeric units of acrylamide (A), bisacrylamide and coupling compound, and
  a cell adhesion molecule; and optionally
  one or more activating agents for activating coupling compound monomeric units for coupling to the cell adhesion molecule.

A seventh aspect of the invention provides a kit comprising;
  acrylamide,
  bisacrylamide,
  a coupling compound,
  one or more polymerisation initiators, a cell adhesion molecule; and optionally,
one or more activating agents for activating coupling compound monomeric units for coupling to the cell adhesion molecule.

In preferred embodiments of these aspects, the coupling compound is 6-acylamidohexanoic acid (6AHA).

In preferred embodiments of these aspects, the mammalian cells may be mammalian progenitor or stem cells.

Other aspects and embodiments of the invention are described in more detail below.

DETAILED DESCRIPTION

Figure 1:
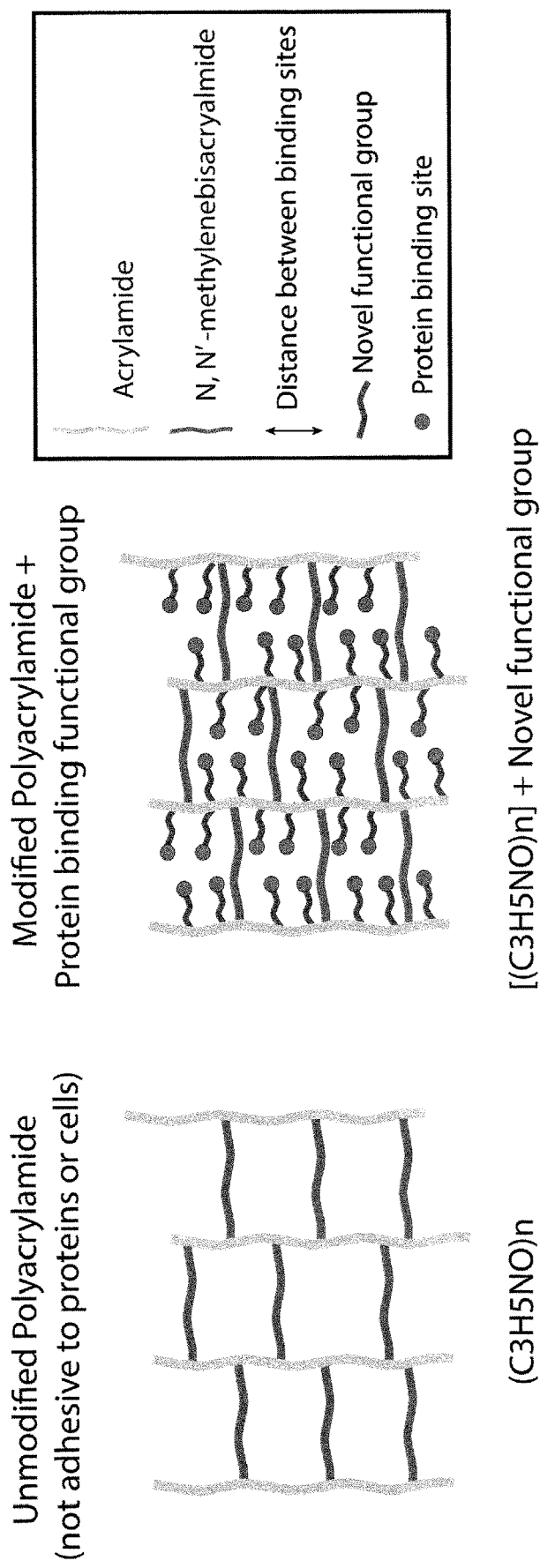
FIG. 1 shows a schematic of a PAAHA co-polymer hydrogel as described herein (right) relative to a standard polyacrylamide hydrogel (left).

This invention relates to substrates for the culture of mammalian cells that have independently tuneable stiffness and density of cell adhesion molecules, such as ECM ligands. The substrates comprise a hydrogel that comprises a co-polymer of monomeric units of acrylamide, bisacrylamide and a coupling compound, such as 6-acylamidohexanoic acid (6AHA: 6-(prop-2-enoylamino) hexanoic acid) (a PA-CC hydrogel). A cell adhesion molecule, such as a component of the extracellular matrix (ECM), is covalently coupled to the coupling compound monomeric units of the hydrogel. A hydrogel described herein may be referred as a StemBond™ hydrogel. The stiffness of the substrate can be controlled without significantly affecting the density of the anchoring sites that bind the cell adhesion molecules by altering the concentration of acrylamide in the hydrogel. The cell adhesion molecule density of the substrate can be controlled without significantly affecting stiffness by altering the concentration of the coupling compound in the hydrogel. This allows the provision of substrates with optimal biochemical and mechanical properties for the culture of mammalian cells, for example for regenerative medicine.

Mammalian cell culture substrates provide a solid or semi-solid surface on which mammalian cells immersed in a culture medium are able to grow and proliferate. The substrates described herein are hydrogels. A hydrogel is a semi-solid material comprising a matrix of polymeric fibres and an aqueous interstitial liquid. Hydrogels are formed by the polymerisation and cross linking of matrix fibres to form a continuous network around the aqueous interstitial liquid which originally held the monomers.

The stiffness and density of cell adhesion molecules in the hydrogels described herein can be controlled independently to produce a cell substrate with any required combination of stiffness and cell adhesion molecule density.

A cell culture substrate as described herein may be produced by a method comprising;
producing a solution of monomers of acrylamide, bisacrylamide, and a coupling compound (CC),
polymerising said monomeric solution to produce a PA-CC co-polymer hydrogel, and
covalently coupling a cell adhesion molecule to the CC monomeric units of the PA-CC co-polymer hydrogel to produce the cell culture substrate.

A polyacrylamide-coupling compound (PA-CC) co-polymer is a hydrogel-forming polymer of cross-linked chains of acrylamide, bisacrylamide and coupling compound monomeric units.

Polyacrylamide (PA) is a hydrogel-forming polymer of cross-linked chains of acrylamide monomeric units. PA gels are well-known in the art. Typically, chains of acrylamide monomeric units in a PA gel are cross-linked using a cross-linking agent, such as bisacrylamide (N, N'-methylenebisacrylamide), which is mixed with acrylamide monomers before polymerisation. Suitable methods for the production of PA hydrogels are well-known in the art.

The proportions of acrylamide and bisacrylamide in the PA-CC co-polymer hydrogel may be adjusted to produce hydrogels that lack surface features, such as creases or cracks. For example, the ratio of acrylamide to bisacrylamide may be from 25:1 to 100:1, preferably about 50:1.

The concentration of the monomeric units of acrylamide in the PA-CC co-polymer hydrogel controls the stiffness of the substrate. Variations in the concentration of acrylamide monomeric units do not significantly affect the density of the cell adhesion molecule. In some embodiments, the concentration of acrylamide monomeric units in the PA-coupling compound co-polymer hydrogel may be varied whilst the concentration of coupling compound is substantially constant. This may allow the optimal stiffness for the growth of particular cells on the substrate under particular conditions to be determined. For example, the ability to adjust substrate stiffness independently of adhesion may be useful in the optimisation of differentiation protocols for a range of different types of progenitor cells.

Monomeric units of acrylamide may be present in the hydrogel in a concentration that provides a pre-determined substrate stiffness. For example, the concentration of monomeric units may provide a hydrogel with a stiffness of 0.1 kPa-100 kPa. This range may reflect the range of stiffness in different biological tissues. For example, a hydrogel with a stiffness of 0.1 to 1.2 kPa may reflect the stiffness of brain tissue, a hydrogel with a stiffness of about 5 to 30 kPa, for example about 10 kPa, may reflect the stiffness of muscle, and a hydrogel with a stiffness of about 50-100 kPa may reflect the stiffness of bone.

The stiffness of a substrate may be determined by any convenient method. For example, the stiffness of fully-hydrated hydrogels may be determined by spherical indentation using a 6 mm diameter tip on a ProLine universal testing machine (Zwick/Roell, Germany). Time-dependent load relaxation may be assessed by first indenting the samples to a depth of 0.1 mm over 10 seconds, followed by a hold over 90 seconds. A poroelastic framework of analysis, (see Strange et al. Applied Physics Letters, 102(3):031913; 2013) may be applied to the data to yield the shear modulus G, hydraulic permeability K, Poisson's ratio v, and viscoelastic ratio R. Typically, two samples per condition may be indented three times each, for a total n of 6.

In some embodiments, the concentration of monomeric units of acrylamide in the PA-CC co-polymer hydrogel may be 2-30% (w/v in g/100 ml; also called % T). Examples of suitable concentrations are shown in Table 1.

Stiffness and/or anchorage density may be homogeneous throughout a substrate described herein or it may be heterogeneous. For example, anchorage density and/or stiffness may be varied across a single substrate. This may be useful for example in the selective growth of different cell populations in different regions of the substrate. This may be useful, for example, in a drug screening system in which the anchorage density and/or stiffness at a location on a substrate at which cells grow, do not grow or die may be correlated with a drug response.

In some embodiments, the concentration of acrylamide monomeric units in the PA-coupling compound co-polymer may provide a hydrogel with a stiffness that corresponds to the stiffness of hard tissue, such as bone. For example, the hydrogel may have a stiffness from 50 kPa to 100 kPa, preferably 80 to 100 kPa, for example about 100 kPa. For example, a hydrogel may comprise 15-20% (w/v) acrylamide monomeric units, preferably 16-17% acrylamide monomeric units. This may be useful in culturing cells, for example stem cells from hard tissue, such as osteogenic and cartilage tissue progenitor cells, as well as other hard tissue cells, such as osteoblasts, osteoclasts and chondrocytes and their precursors and anchorage dependent cells.

In other embodiments, the concentration of acrylamide monomeric units in the PA-coupling compound co-polymer may provide a hydrogel with a stiffness that corresponds to the stiffness of intermediate tissue, such as muscle. For example, the hydrogel may a stiffness from 5 kPa to 30 kPa, for example 5 kPa to 15 kPa or 20 kPa to 30 kPa. For example, a hydrogel may comprise 10 to 15% (w/v) acrylamide monomeric units. This may be useful in culturing cells, for example stem cells from intermediate tissue, such as muscle. Suitable cells include myocytes, fibroblasts, differentiated mesenchymal cells and precursors and progenitors thereof and anchorage dependent cells.

In other embodiments, the concentration of acrylamide monomeric units in the PA-coupling compound co-polymer may provide a hydrogel with a stiffness that corresponds to the stiffness of soft tissue, such as embryo or brain. For example, the hydrogel may a stiffness from 0.1 kPa to 1.2 kPa, preferably about 0.4 kPa. For example, a hydrogel may comprise 1 to 10% (w/v) acrylamide monomeric units, preferably 2.8-5.0% acrylamide monomeric units. This may be useful in culturing cells, for example stem cells from soft tissue, such as embryonic stem cells, and organoids. Suitable stem cells are described in more detail below. Other suitable cells include cancer cells, anchorage independent cells, epithelial cells, and neural cells.

The co-polymeric fibres that form the scaffold of the hydrogels further comprise monomeric units of the coupling compound. The presence of coupling compound monomeric units allows the covalent attachment of adhesion molecules to the hydrogel.

Suitable coupling compounds include compounds of Formula 1;

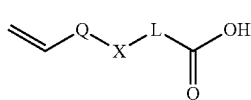

Formula 1 wherein
L is selected from optionally substituted $C_{2-10}$ alkylene, optionally substituted $C_{2-10}$ alkenylene, —(O—CR$_2$)$_n$— and —(CR$_2$—O)$_n$— wherein n is an integer from 1 to 4;
Q is selected from —C(=O)—, —C(R$_2$)— and —C(R)=C(R)—; and
X is selected from —O—, —S—, —C(R$_2$)—, —C(R)=C(R)—, and —N(R)—.

Preferably, L is selected from optionally substituted $C_{4-7}$ alkylene, optionally substituted $C_{4-7}$ alkenylene, and —(CR$_2$—O)$_n$— wherein n is an integer from 1 to 2. More preferably, L is optionally substituted $C_{2-10}$ alkylene and even more preferably optionally substituted $C_{4-7}$ alkylene.

In some embodiments, the compound of Formula 1 is a compound of Formula 1a:

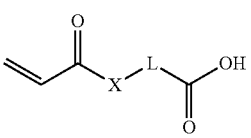

Formula 1a wherein
L is selected from optionally substituted $C_{2-10}$ alkylene, optionally substituted $C_{2-10}$ alkenylene, —(O—CR$_2$)$_n$— and —(CR$_2$—O)$_n$— wherein n is an integer from 1 to 4; and
X is selected from —O—, —S—, —C(R$_2$)—, —C(R)=C(R)—, and —N(R)—.

Preferably, X is —O— or —N(R)—, more preferably —N(R)—, for example —N(H)—.

Preferably, L is selected from optionally substituted $C_{4-7}$ alkylene, optionally substituted $C_{4-7}$ alkenylene, —(O—CR$_2$)$_n$— and —(CR$_2$—O)$_n$— wherein n is an integer from 1 to 2. More preferably, L is optionally substituted $C_{2-10}$ alkylene and even more preferably optionally substituted $C_{4-7}$ alkylene.

In some cases, X is —O— or —N(R)— and L is selected from optionally substituted $C_{4-7}$ alkylene, optionally substituted $C_{4-7}$ alkenylene, —(O—CR$_2$)$_n$— and —(CR$_2$—O)$_n$— wherein n is an integer from 1 to 2. In these cases, L is preferably optionally substituted $C_{4-7}$ alkylene. In these cases X is preferably —N(R)—, for example —N(H)—.

Examples of suitable coupling compounds include 6-acrylamidohexanoic acid and 2-carboxyethyl acrylate.

Preferably, the coupling compound is 6-acrylamidohexanoic acid (6AHA: CAS 20766-85-2; PubChem CID 324200; 6-(prop-2-enoylamino) hexanoic acid). 6AHA is readily available from commercial suppliers.

The phrase "optionally substituted" as used herein, pertains to a parent group which may be unsubstituted or which may be substituted with one or more groups independently selected from —F, —Cl, —Br, —I, —OH, —OR' or —NR'R', wherein each R' is independently selected from H, a $C_{1-7}$ alkyl or, in the case of the amino group, both R' groups taken together with the nitrogen atom to which they are attached, may form a heterocyclic ring having from 4 to 8 ring atoms.

$C_{1-10}$ alkylene: The term "$C_{1-10}$ alkylene" as used herein, pertains to a divalent moiety obtained by removing a hydrogen atom from each of two carbon atom of a hydrocarbon compound having from 1 to 10 carbon atoms, which may be linear or branched, and which may be saturated or unsaturated (e.g. partially unsaturated, fully unsaturated). Thus, the term "alkyl" includes the sub-classes alkenyl, alkynyl, etc., discussed below.

Examples of saturated alkylene groups include, but are not limited to, methylene ($C_1$), ethylene ($C_2$), propylene ($C_3$), butylene ($C_4$), pentylene ($C_5$), hexylene ($C_6$) and heptylene ($C_7$).

Examples of saturated linear alkyl groups include, but are not limited to, methylene ($C_1$), ethylene ($C_2$), n-propylene ($C_3$), n-butylene ($C_4$), n-pentylene (amyl) ($C_5$), n-hexylene ($C_6$) and n-heptylene ($C_7$).

Examples of saturated branched alkyl groups include iso-propylene ($C_3$), iso-butylene ($C_4$), sec-butylene ($C_4$), tert-butylene ($C_4$), iso-pentylene ($C_5$), and neo-pentylene ($C_5$).

$C_{2-10}$ Alkenylene: The term "$C_{2-10}$ alkenylene" as used herein, pertains to an alkylene group having one or more carbon-carbon double bonds.

Examples of unsaturated alkenylene groups include, but are not limited to, ethenylene (vinylene, —CH=CH—), 1-propenylene (—CH=CH—CH$_2$—), 2-propenylene (allylene, —CH—CH=CH—), isopropenylene (1-methylvinylene, —C(CH$_3$)=CH—), butenylene ($C_4$), pentenylene ($C_5$), and hexenylene ($C_6$).

Each R group is independently selected from H, —F, —Cl, —Br, —I, —OH, —OR' or —NR'R', wherein each R' is independently selected from H, a $C_{1-7}$ alkyl or, in the case of the amino group, both R' groups taken together with the nitrogen atom to which they are attached, may form a heterocyclic ring having from 4 to 8 ring atoms. Preferably, R is H.

$C_{1-7}$ alkyl: The term "$C_{1-7}$ alkyl" as used herein, pertains to a monovalent moiety obtained by removing a hydrogen atom from a carbon atom of a hydrocarbon compound having from 1 to 7 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

In some embodiments, all of the available coupling compound monomeric units in the hydrogel are covalently bound to cell adhesion molecules.

The concentration of the coupling compound in the hydrogel may determine the density of the cell adhesion molecule in the substrate. An increased concentration of the coupling compound, for example, provides an increased number of attachment sites for the cell adhesion molecule. For small cell adhesion molecules, including amino acid epitopes such as RGD-NH2, the concentration of coupling compound may correspond directly to the amount of cell adhesion molecule coupled to the substrate. For larger cell adhesion molecules, such as fibronectin and collagen, which may bind to more than one monomeric unit of the coupling compound, the amount of cell adhesion molecule on the substrate may be less dependent on the concentration of coupling compound.

Monomeric units of the coupling compound may be present in the hydrogel in a concentration that provides a pre-determined density of the cell adhesion molecule. For example, the concentration of monomeric units may provide a hydrogel with a density of the cell adhesion molecule of 40K to 250K per $\mu m^2$. This range may reflect the density of the cell adhesion molecule in different biological tissues. For example, the concentration of monomeric units of coupling compound in the hydrogel may be 10 to 100 mM, preferably 20 to 90 mM. In some embodiments, the concentration of monomeric units of coupling compound in the hydrogel may be 32 to 70 mM, for example 40 to 60 mM, In other embodiments, the concentration of monomeric units of coupling compound in the hydrogel may be 70 to 100 mM, for example 70 to 90 mM.

The concentration of coupling compound in a hydrogel may be determined by the type of cell to be cultured. A substrate with a low adhesion molecule density may provide a low adhesion environment that is useful for example for culturing stem cells that tend to grow in spheroids. For example, stem cells may be cultured on substrates comprising 40-70 mM coupling compound, preferably about 50 mM. A substrate with a high adhesion molecule density may provide a high adhesion environment that is useful for example for culturing progenitor cells that are native to niches with a high density of ECM, such as bone. For example, osteogenic progenitor cells may be cultured on substrates comprising 70-100 mM, for example 70-90 mM coupling compound, preferably about 80 mM.

Variations in the concentration of coupling compound do not significantly affect stiffness. In some embodiments, the concentration of coupling compound monomeric units in the hydrogel may be varied whilst the concentration of acrylamide monomeric units is substantially constant. This may allow the optimal density of the cell adhesion molecule for particular cells under particular conditions to be determined.

Examples of methods for the production of PA-6AHA and other PA-CC polymers are described elsewhere herein.

The monomeric solution may be polymerised in a glass or plastic mould to produce a hydrogel of a defined shape.

The hydrogel may be of any shape or thickness, depending on the application. For example, in some embodiments, the substrate may be in the form of a disk or sheet of 200 µm of less that forms or is placed on the bottom of a well-plate or flask.

In some embodiments, the hydrogel may be attached to a solid support. For example, the hydrogel may be covalently attached to a solid surface, such as glass or plastic. This may be useful in reducing or restraining gel swelling.

Following production of a hydrogel comprising a PA-coupling compound co-polymer, the hydrogel may be coupled to a cell adhesion molecule to produce a mammalian cell culture substrate or stored, for example at 4° C., for use in subsequent production of a mammalian cell culture substrate.

A cell adhesion molecule is a molecule that binds to the surface of cells through cell adhesion. Cell adhesion molecules may include ligands of cell surface receptors, such as integrins, cadherins and selectins. Suitable cell adhesion molecules include components of the extracellular matrix (ECM). An ECM component is a protein, glycoprotein, oligosaccharide or proteoglycan that is present in the mammalian extracellular matrix. Suitable ECM components bind to mammalian cells and form a cell anchorage point in the ECM. For example, the ECM component may be a ligand that binds a cell surface receptor, such as an integrin. Preferably, the ECM component is an amine containing molecule, such as a protein or peptide. In some embodiments, the ECM may comprise an RGD motif or other amino acid sequences (e.g. IKAV) which mediates cell attachment (Ruoslahti et al (1996) Ann Rev Cell Dev Biol 12 697-715). Suitable ECM components include fibronectin, collagen, fibrinin, laminin, tenascin, vitronectin and thrombospondin. In some embodiments, the cell adhesion molecule that is coupled to the coupling compound may be selected depending on the cell or tissue type under study.

A cell adhesion molecule for use as described herein may include a primary amine (—NH2) group that is reactive with the free carboxyl groups in the co-polymer. This allows the attachment of the cell adhesion molecule to the coupling compound monomeric units of the co-polymer.

In some embodiments, the cell adhesion molecule may be a synthetic molecule, such as a peptide. The sequence of a peptide cell adhesion molecule may match an available cell surface receptor, such as an integrin, on the cell type to be cultured on the substrate. A substrate may thus be selective for cells that display a cell surface receptor that binds to the cell adhesion molecule.

In some embodiments, a mixture of two or more different cell adhesion molecules may be coupled to the hydrogel to produce the cell substrate.

The density of cell adhesion molecule on a substrate may be determined using standard analytical techniques, such as fluorescence microscopy, super-resolution microscopy (SRM), atomic force microscopy (AFM) or two step sandwich type ELISA or enzymatic reactions.

Cell adhesion molecules may be obtained from commercial suppliers or produced by recombinant or synthetic means using standard techniques.

The cell adhesion molecule may be covalently coupled to the coupling compound monomeric units of the PA-coupling compound co-polymer by any convenient method. The coupling compound monomeric units of the hydrogel provide free carboxyl or carboxylic acid groups that are particularly suitable for use in coupling to the cell adhesion molecule. In some embodiments, the carboxyl/carboxylic acid groups of the coupling compound monomeric units may be activated before coupling to the cell adhesion molecule.

Suitable methods for activating carboxyl/carboxylic acid groups for chemical coupling are well known in the art. For example, the coupling compound carboxyl/carboxylic acid groups may be activated by contacting the hydrogel with one or more activating agents, such as N-(3-Dimethylaminopropyl)-N'-ethylcarbodiimide hydrochloride (EDAC) and N-hydroxysuccinimide (NHS) or sulfo-NHS. Reaction with the activating agent converts the carboxyl groups into an amine reactive form, such as an NHS ester or sulfo-NH ester, which is reactive with a primary amine of the cell adhesion molecule to form a covalent bond. For example, the amine reactive intermediates may react with the N terminal primary amine of an adhesion molecule.

Other suitable coupling methods are available in the art.

Following covalent attachment of the cell adhesion molecule to the coupling compound monomeric units, the substrate may be immersed in cell culture medium and used for cell culture or stored for subsequent use.

A cell culture medium is a nutritive solution that supports the growth and proliferation of mammalian cells. The substrates are not limited to any specific cell culture medium and any media may be used to culture cells on the substrate. Suitable cell culture media are well known in the art.

In some embodiments, the cell culture medium may be an undefined medium. An undefined medium may contain one or more undefined components or constituents, such as feeder cells, stromal cells, serum, matrigel, serum albumin and complex extracellular matrices. In some embodiments, a cell culture medium may comprise serum and leukaemia inhibitory factor (LIF).

In some embodiments, the cell culture medium may be a defined medium. A defined medium contains only specified components, preferably components of known chemical structure and is devoid of undefined components or constituents, such as feeder cells, stromal cells, serum, matrigel, serum albumin and complex extracellular matrices. In some embodiments, the defined medium is humanised. A humanised defined medium is devoid of components or supplements derived or isolated from non-human animals, such as Foetal Bovine Serum (FBS) and Bovine Serum Albumin (BSA), and mouse feeder cells. Conditioned medium includes undefined components from cultured cells and is not defined.

A medium may comprise a defined basal medium supplemented with a serum-free media supplement and/or one or more additional components, for example transferrin, 1-thioglycerol, 2-mercaptoethanol, FGF2, defined lipids, L-Gln, non-essential amino acids, and optionally polyvinyl alcohol; polyvinyl alcohol and insulin; serum albumin; or serum albumin and insulin.

Suitable chemically defined basal medium, such as Advanced Dulbecco's modified eagle medium (DMEM) (Price et al Focus (2003) 25 3-6), Knockout Dulbecco's Modified Eagle's Medium (KO-DMEM), DMEM/F12, Iscove's Modified Dulbecco's medium (IMDM) and RPMI-1640 (Moore, G. E. and Woods L. K., (1976) Tissue Culture Association Manual. 3, 503-508) are known in the art and available from commercial sources (e.g. Sigma-Aldrich MI USA; Life Technologies USA).

Serum-free media supplements, such as N2, B27 and N21, are well known in the art and widely available commercially (e.g. Invitrogen; Sigma Aldrich Inc.). Suitable serum-free media supplements include B27 (Brewer et al Brain Res (1989) 494 65-74; Brewer et al J. Neurosci Res 35 567-576 (1993); Brewer et al Focus 161 6-9; Brewer et al (1995) J. Neurosci. Res. 42:674-683; Roth et al J Trace Elem Med Biol (2010) 24130-137), N2 (Lee et al (2000) Nat Biotechnol 18(6) 675-679; Lumelsky et al (2001) Science 292(5520): 1389-1394) and NS21 (Chen et al J. Neurosci Meths (2008) 171 239-247). In some embodiments, a suitable defined medium may comprise N2 and B27.

The medium may be a stem cell medium which supports the growth of stem cells without loss of potency. Examples of stem cell media include CDM-PVA (Johansson and Wiles (1995) Mol Cell Biol 15, 141-151), which comprises a basal medium supplemented with polyvinyl alcohol, insulin, transferrin and defined lipids. For example, a CDM-PVA medium may consist of: 50% Iscove's Modified Dulbecco's Medium (IMDM) plus 50% Ham's F12 with GlutaMAX-1m or 50% F12 NUT-MIX (Gibco, supplemented with 1% chemically defined lipid concentrate, 450 µM 1-thiolglycerol, 15 µg/ml transferrin, 1 mg/ml polyvinyl alcohol, 7 µg/ml insulin. Other suitable chemically defined nutrient media include hESC maintenance medium (CDMA) which is identical to the CDM-PVA described above with the replacement of PVA with 5 mg/ml BSA; and RPMI basal medium supplemented with B27 and Activin (for example at least 50 ng/ml). Other suitable media are described in Valier et al 2009 Stem Cells 27: 2655-2666, Touboul 2010 51:1754-1765. Teo et al 2011 Genes & Dev. (2011) 25: 238-250 and Peterson & Loring Human Stem Cell Manual: A Laboratory Guide (2012) Academic Press.

In some embodiments, the medium may be a minimal defined medium.

A cell culture system as described herein may comprise a substrate as described herein, cell culture medium and mammalian cells.

Any mammalian cell type may be cultured on a substrate as described herein. Suitable mammalian cells include human cells and cells from laboratory models, such as mouse and rat.

Suitable mammalian cells include epithelial cells, endothelial cells, neural cells, fibroblasts, such as human dermal or tendon fibroblasts, stromal cells, such as bone marrow derived stromal cells and smooth muscle cells, cancer cells, progenitor and precursor cells, iPSCs, spheroid forming cells, colony forming cells, anchorage independent cells, and embryonic, foetal and adult stem cells.

Stem cells are undifferentiated or partially differentiated cells that are capable of self-renewal and differentiation into one or more specialized cell-types. Stem cells may be pluripotent, multipotent, oligopotent or unipotent and may include embryonic stem cells (ESCs) and non-embryonic stem cells, for example foetal stem cells, adult stem cells, amniotic stem cells, cord stem cells and induced pluripotent stem cells (iPSCs). In some embodiments, the PSCs are not human embryonic stem cells.

The stem cells may be obtained from mammals at any developmental stage, including foetal, neonatal, juvenile, mature or aged.

Suitable stem cells include corneal (limbal) stem cells; oligodendrocyte progenitor cells (OPCs); embryonic stem cells; mesenchymal stem cells, adipose-derived stem cells, endothelial stem cells, dental pulp stem cells, skin epidermal stem cells; gut (intestinal) stem cells; orogenital stem cells; bronchial and other epithelial stem cells; muse cells, haematopoletic stem cells, amniotic stem cells bone marrow stromal stem cells; growth plate stem cells and iPSCs.

Progenitor and precursor cells are partially differentiated cells that are capable of differentiation into one or more specialized cell-types. Suitable precursor cells include oligodendrocyte progenitor cells.

Suitable techniques for cell culture are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430) Basic Cell Culture Protocols' by J. Pollard and J. M. Walker (1997), 'Mammalian Cell Culture: Essential Techniques' by A. Doyle and J. B. Griffiths (1997), 'Human Embryonic Stem Cells' by A. Chiu and M. Rao (2003), Stem Cells: From Bench to Bedside' by A. Bongso (2005), Peterson & Loring (2012) Human Stem Cell Manual: A Laboratory Guide Academic Press and 'Human Embryonic Stem Cell Protocols' by K. Turksen (2006). Media and ingredients thereof may be obtained from commercial sources (e.g. Gibco, Roche, Sigma, Europa bioproducts, R&D Systems). Standard mammalian cell culture conditions may be employed for the above culture steps, for example 37C, 21% Oxygen, 5% Carbon Dioxide. Media is preferably changed every two days and cells allowed to settle by gravity.

Other aspects of the invention provide reagents and kits for producing substrates for mammalian cell culture. A kit may comprise;
  (i) a substrate comprising a polyacrylamide-coupling compound (PA-CC) co-polymer hydrogel and a cell adhesion molecule, said cell adhesion molecule being covalently coupled to coupling compound monomeric units of the hydrogel;
  (ii) a PA-CC co-polymer hydrogel; a cell adhesion molecule; and one or more activating agents, optionally EDAC and NHS; or
  (iii) coupling compound; acrylamide; a cross-linking agent, optionally bisacrylamide; one or more polymerisation initiators, optionally APS and TEMED; a cell adhesion molecule; and one or more coupling agents, optionally EDAC and NHS.

A kit may further comprise a mould for casting a PA-CC co-polymer hydrogel.

A kit may further comprise one or more cell culture media. The one or more culture media in the kit may be formulated in deionized, distilled water. The one or more media will typically be sterilized prior to use to prevent contamination, e.g. by ultraviolet light, heating, irradiation or filtration. The one or more media may be frozen (e.g. at −20° C. or −80° C.) for storage or transport. The one or more media may contain one or more antibiotics to prevent contamination.

The one or more media may be a 1× formulation or a more concentrated formulation, e.g. a 2× to 250× concentrated medium formulation. In a 1× formulation each ingredient in the medium is at the concentration intended for cell culture, for example a concentration set out above. In a concentrated formulation one or more of the ingredients is present at a higher concentration than intended for cell culture. Concentrated culture media are well known in the art. Culture media can be concentrated using known methods e.g. salt precipitation or selective filtration. A concentrated medium may be diluted for use with water (preferably deionized and distilled) or any appropriate solution, e.g. an aqueous saline solution, an aqueous buffer or a culture medium.

The reagents in the kit may be contained in hermetically-sealed vessels. Hermetically-sealed vessels may be preferred for transport or storage of the reagents to prevent contamination. The vessel may be any suitable vessel, such as a flask, a plate, a bottle, a jar, a vial or a bag.

Substrates described herein with defined stiffness may be useful in the selection of cells from specific tissues. For example, a substrate with high stiffness may be used to select cells that originate from hard tissue, such as bone. A substrate with low stiffness may be used to select cells that originate from soft tissue, such as brain.

In some embodiments, a substrate with low stiffness may be used to select anchorage independent cells, such as cancer cells. A cell population may be cultured on a substrate described herein having a stiffness of 0.1 to 1.2 kPa. This causes the programmed cell death of anchorage dependent cells in the population (via anoikis). Culturing on the soft substrate is therefore selective for anchorage independent cells.

Substrates described herein with a defined density of cell adhesion molecules may be useful in the selection of cells from specific tissues. For example, a substrate with a high density of cell adhesion molecules may be used to select cells that originate from a high adhesion environment, such as bone or other hard tissue. A substrate with a low density of cell adhesion molecules may be used to select cells that originate from a low adhesion environment, such as brain or other soft tissue.

The invention also provides methods of generating cell-selective substrates by optimising the stiffness and/or adhesion molecule density for a population of target cells. A method may comprise;
  providing a set of substrates as described above, each substrate in the set having a different stiffness and/or density of cell adhesion molecules relative to the other substrates in the set;
  measuring the growth of a population of target cells on each substrate in the set of substrates, and
  identifying the substrate in the set that supports the highest growth of the target cells.

Suitable target cells are described above and include stem and progenitor cells from any tissue.

In some embodiments, the growth of the population of target cells on each substrate in the set of substrates may be compared to the growth of the population of control cells on each substrate. The substrate that supports the highest growth of the target cells relative to the control cells may be identified.

Cell growth may be determined by any convenient technique.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (ii) A and B, just as if each is set out individually herein.

EXPERIMENTAL

Materials and Methods

Circular glass coverslips of any diameter and thickness (typically 20 mm ø, 22 mm ø, 25 mm ø or 32 mm ø and No. 1 thickness) were placed in metal racks and washed three times in MilliQ water, then 70% ethanol, followed by 0.2% v/v sodium hydroxide. Clean glass coverslips were then placed in large parafilm coated dishes (10 cm ø) and wiped to remove any residues. The cover glasses were then treated with γ-methacryloxypropyltrimethoxysilane (also known as [3(Methacryloyloxy)propyl]trimethoxysilane; $C_{10}H_2OOSi$; Bind Saline, GE Healthcare) dissolved in ethanol with 5% v/v acetic acid. This solution was left to incubate for 2 hours at room temperature until almost all the ethanol had evaporated. The coverslips were then wiped with a lint free tissue (Kimwipe, KimTech) and briefly rinsed in MilliQ water. The reactive coverslips were then dried and polished with a lint free tissue. After treatment, these reactive coverslips present a chemical group which allows covalent bonding of the hydrogel to the glass upon gel polymerisation. This restrains gel swelling when the gel is immersed in solution. Coverslips of the same diameter were washed as above and treated to become highly hydrophobic via incubation in siliconizing fluid diluted in chloroform (e.g. Surfacil). After a 1 hour incubation, the hydrophobic coverslips were dried, wiped clean and laid on lint free tissue (Kimwipes).

Polyacrylamide and 6-acrylamidohexanoic acid ($C_9H_{15}NO_3$) co-polymer hydrogels ('StemBond™ gels') were synthesised as per the table below. 6-acrylamidohexanoic acid (also known by IUPAC name 6-(prop-2-enoylamino) hexanoic acid) was first dissolved in 100% methanol to a stock concentration of 2M. The recipes below make a 507.5 µl aliquot of gel solution after the addition of the chemical initiators of free-radical polymerisation (APS and TEMED); this equates to three-five gels.

TABLE 1

Polyacrylamide and 6-acrylamidohexanoic acid co-polymer recipes.

| Ingredient | Stock concentration | 'Soft' gel (final conc) | Stiff gel (final conc) |
| --- | --- | --- | --- |
| Approximate stiffness | — | 0.5 kPa | 30.0 kPa |
| Acrylamide:Bisacrylamide (ratio) | — | 50.4:1 | 57.8:1 |
| Acrylamide | 40% in $H_2O$ | 35 ul (388.1 uM) | 200 ul (2217.7 uM) |
| N,N'-methylenebisacrylamide | 2% in $H_2O$ | 30 ul (7.7 uM) | 150 ul (38.4 uM) |
| Acryloyl 6-hexanoic acid | 2M in methanol (99%) | 12 ul (50 mM) | 12 ul (50 mM) |
| Ammonium persulfate | 10% (w/v) | 5 ul | 5 ul |
| N,N,N',N'-Tetramethylethylenediamine | 99% | 2.5 ul | 2.5 ul |
| $H_2O$ (up to 507.5 ul) | — | 423 ul | 138 ul |

A concentration of 48-50 mM of 6-Acylamidohexanoic Acid (12 µl from 2M stock in 500 µl final) in combination with the above soft gel recipe is optimal for maintaining naïve pluripotency. Altering 6-Acylamidohexanoic Acid concentration in the above hydrogels can be used to modify the number of ligand binding sites in the gel and thus cell or molecule binding/adhesion. Interestingly, within defined limits, cell adhesion and mechanotransduction can be modulated without substantial alterations in stiffness.

Once the gel solutions were made, but before the addition of APS and TEMED, they were degassed in a vacuum chamber for 10 minutes, to reduce oxygen within the solution which could inhibit the polymerization reaction if made in a container with low head space (otherwise degassing is not essential). The initiators APS and TEMED were then added in the amounts shown to the 500 µl aliquot of gel solution to begin the polymerisation reaction and a small drop of the StemBondc™ hydrogel gel mixture was added to the centre of the γ-methacryloxypropyltrimethoxysilane treated coverglass which was situated in a large parafilm coated dish. The hydrophobically treated 'top' coverglass was then immediately dropped on to the polymerising gel mixture; this spread the mixture evenly between the two coverslips. After 15 minutes of polymerisation the top coverslip was removed with forceps and hydrogels were rinsed twice in 100% methanol before being immersed multiple times in large volumes of PBS. Hydrogels were then be stored in PBS in the fridge at 4° C. until required. At this stage gels may be stored at 4° C. or even room temperature for at least a month or more without discernible loss of properties.

On the day of conjugation, StemBond™ hydrogels were rinsed twice and fully hydrated in MES buffer (0.1 M 2-(N-morpholino) ethanesulfonic acid, 0.5 M sodium chloride, pH 6.1 (Sigma-Aldrich, St. Louis, Mo.)). To activate the surface carboxyl groups of the 6-Acylamidohexanoic Acid, which were co-polymerised into the gel-network, 500-1000 µl of a 0.2M N-(3-Dimethylaminopropyl)-N'-ethylcarbodiimide hydrochloride (EDAC) and 0.5M N-hydroxysuccinimide (NHS) solution in MES buffer (pH 6.1) was pipetted on to the surface of the PABAHA hydrogels which were still situated in a parafilm coated dish. They were left to incubate in this solution at room temperature for 30 minutes.

Immediately after this, the hydrogels were washed with 60% methanol in PBS (Ph 7.2). Methanol was aspirated away and the functionalised gels were then reacted with the primary amines (NH2 groups) of human plasma fibronectin (100-300 µg/ml) in HEPES buffer pH 8.5 overnight at 4° C. through a dehydration condensation reaction (note: it was not necessary to incubate overnight as the reaction was completed within minutes-hours). Alternatively, the functionalised gels were then reacted with the primary amines (NH2 groups) of human laminin (50 µg/ml) in HEPES buffer pH 8.2 overnight at 4° C. After the fibronectin or laminin had been covalently linked to the surface of the hydrogel, any remaining active NHS groups were 'blocked' via addition of ethanolamine in HEPES buffer (50 mM) pH8.5. These PA6AHA hydrogels were then placed in culture plates and immersed in the desired culture medium. The plates containing the gels were then placed in the 37° C. incubator for 1 hour to pre-equilibrate. After this pre-equilibration period fresh pre-warmed culture medium was added and the cells were plated at the desired density.

Results

Figure 2:
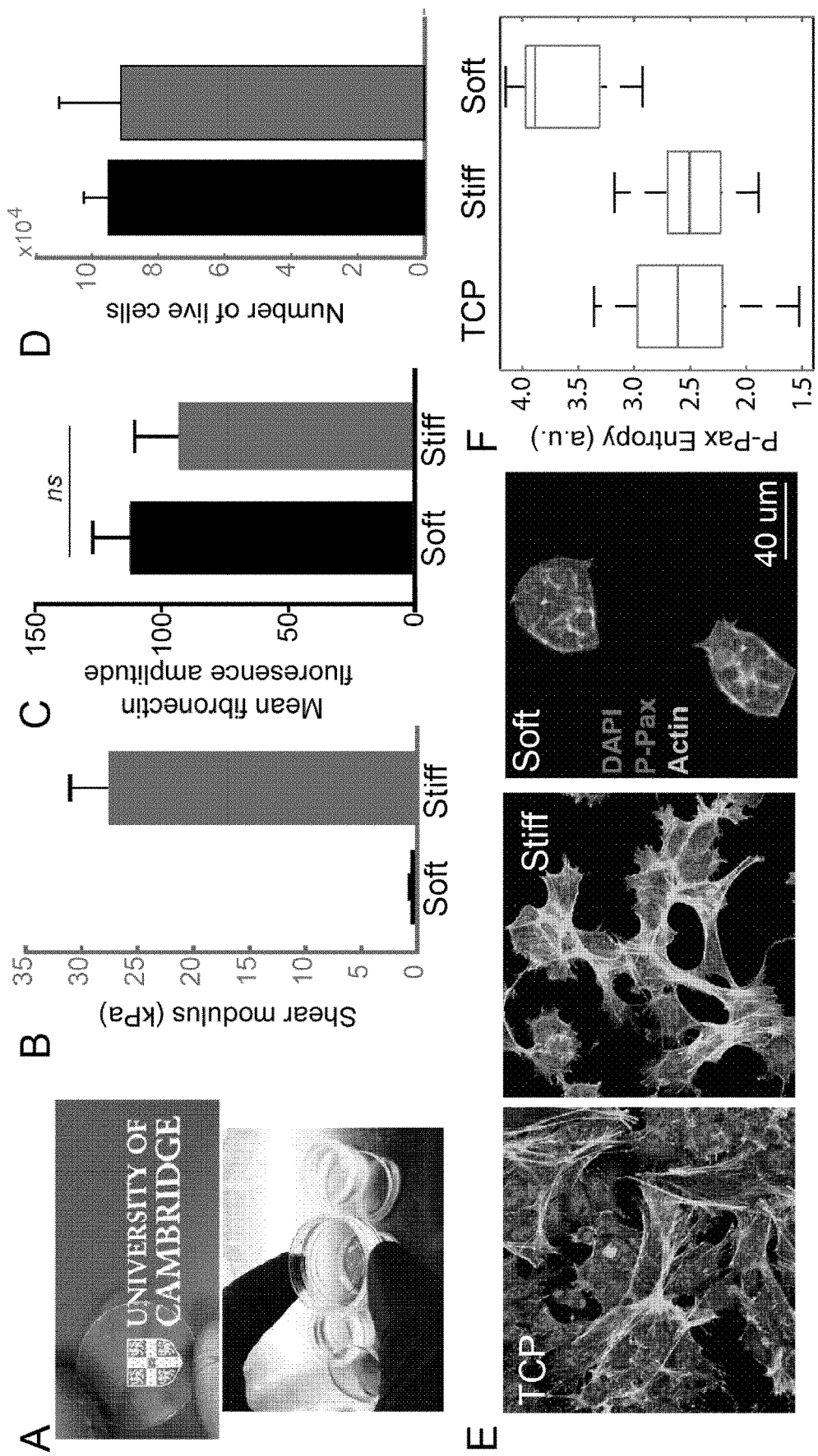
FIG. 2 shows the characteristics of PA6AHA co-polymer hydrogel as described herein. (A) The prototype imaging-compatible PA6AHA co-polymer hydrogel. The top panel demonstrates the optical clarity of the gels by showing the logo below the hydrogel. The bottom demonstrates that the hydrogels can be used in any tissue culture dish. (B) The soft hydrogel (Soft) was designed to approximate the stiffness as early embryo and brain tissue. (C) Soft and stiff hydrogels (Stiff) can be developed to have exactly the same ECM density. For the hydrogel prototype used in both studies described, ES cells attach as well on Soft as they do on Stiff (D). (E) ES cells spread and form organised focal adhesions (as seen by phosphorylated Paxillin, or P-Pax, which is a measure of focal adhesion maturation) on tissue culture plastic (TCP) and Stiff, while they form tight aggregates reminiscent of the early embryo on Soft, with less abundant and more disorganised focal adhesions. (F) The organisation of focal adhesion is measured by the Entropy of P-Pax, showing that Soft promotes more disorganised formation of focal adhesions than Stiff and TCP indicating less mature focal adhesions.

Fully functionalisable stem cell substrates were developed from hydrogels of a co-polymer of PA and 6APA (FIG. 1). These gels could be mechanically tuned across a wide range of physiological stiffness ranging from embryo/brain stiffness to skeletal stiffness (FIG. 2B). Uniquely, and in addition, we integrated a versatile functional group that could be exploited to control the density of covalently linked ECM anchorage points without significant alteration in stiffness within a defined range. Practically, this meant that the same ECM density and composition could be presented to a stem cell culture on both soft and stiff substrates (FIG. 2C), meaning that the effects of mechanics, ligand anchoring and density of binding motifs, on stem cell function could be isolated. Importantly, this allowed us to independently change ECM density and composition without altering stiffness. To date, these important drivers of stem cell function have never been systematically decoupled; the hydrogel system described herein allowed this decoupling and unlocked an optimal stem cell culture system. At the same time, the ability to control cell-ECM adhesion independently of stiffness solved another problem that has inhibited the use of hydrogel technology for stem cell culture which is that until now, stem cells from soft tissue have not adhered well to soft hydrogels. As shown in FIG. 2, stem cells were found to adhere just as well to soft substrates as they did to stiff substrates (FIG. 2D). Ours is a highly flexible biotechnological tool that is compatible with any existing tissue culture substrate (FIG. 2A) and can be functionalised with any ECM protein with specified density for independent control over ECM composition and stiffness. It is also entirely compatible with imaging.

Figure 3:
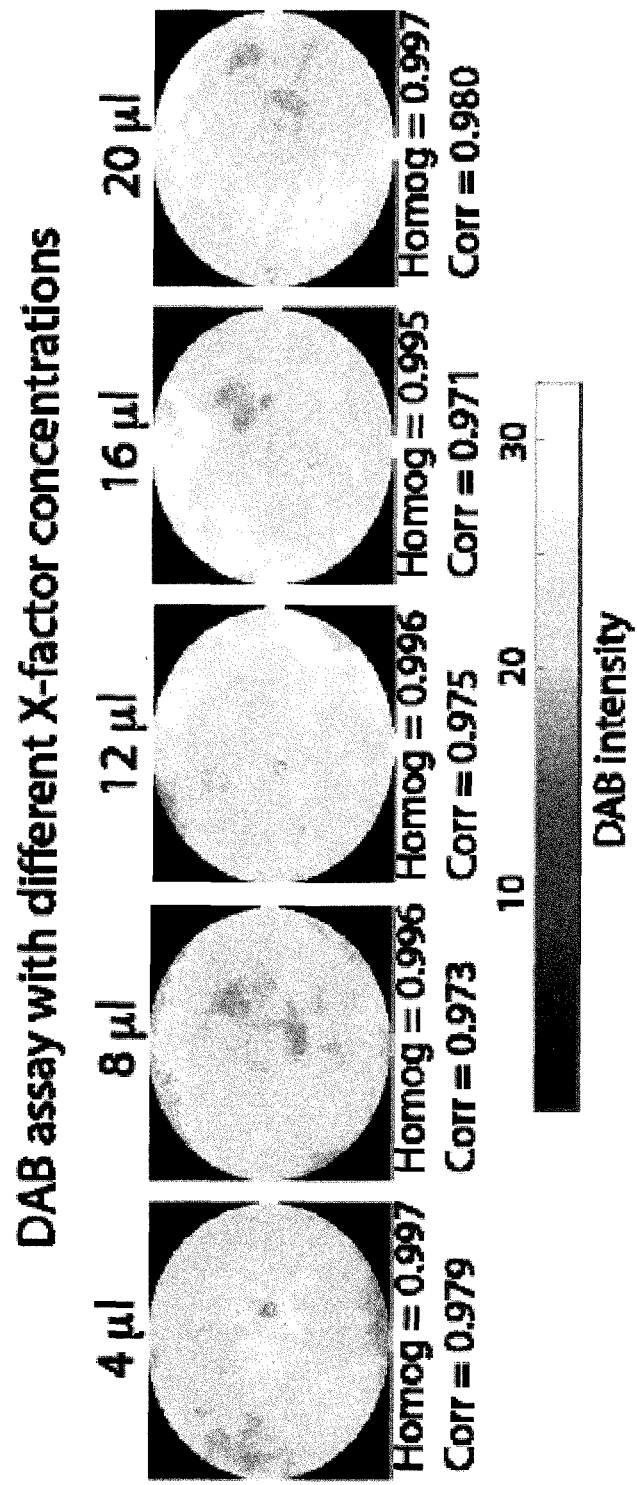
FIG. 3 shows the results of a metal enhanced diaminobenzidine (DAB) assay to test for immobilisation of fibronectin and its homogeneity on the hydrogels surface with different amounts of AHA.
Figure 4:
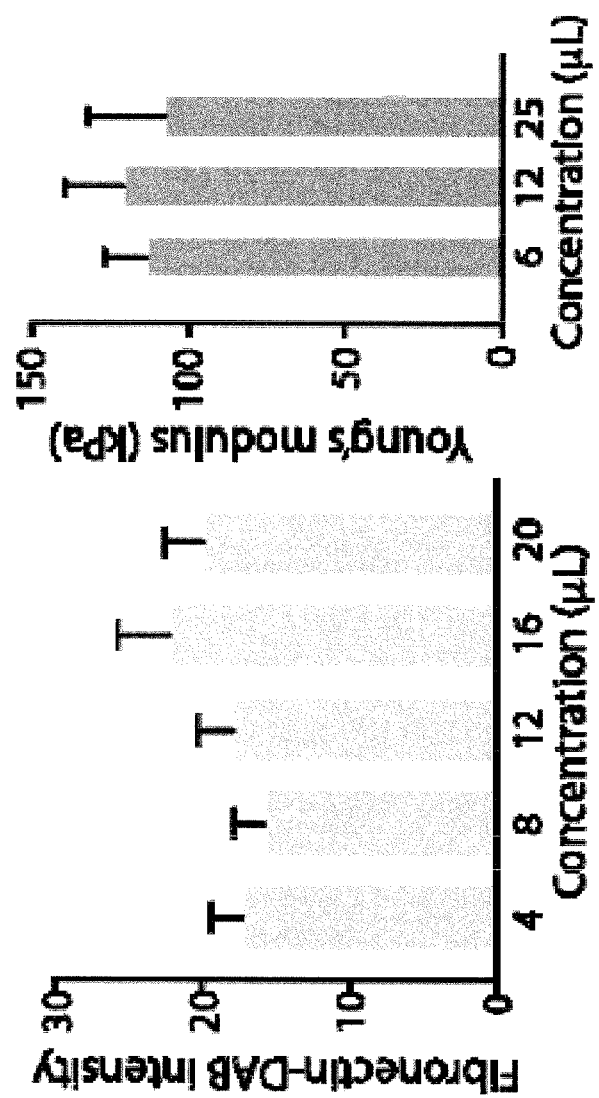
FIG. 4 shows a graph of diaminobenzidine (DAB) intensity (left) and stiffness (right) as determined by nanoindentation for hydrogels containing different amounts of 6AHA.

A diaminobenzidine (DAB) assay was used to test for homogeneity and intensity of fibronectin on the hydrogels described herein. Fibronectin was found to be highly homogeneous on the gels independent of how much of the 6AHA is used, and the amount of fibronectin does not vary across concentration of 6AHA (FIG. 3, FIG. 4 left). Nanoindentation was also used to show that the hydrogels do not vary in stiffness across concentration of BAHA (FIG. 4 right). A panel of genes was probed for differences due to concentration of 6AHA. Naïve pluripotent genes (KLF4 and ESRRB) did not change with matrix tethering, but other genes (TAGLN and Lefty2) did.

Figure 5:
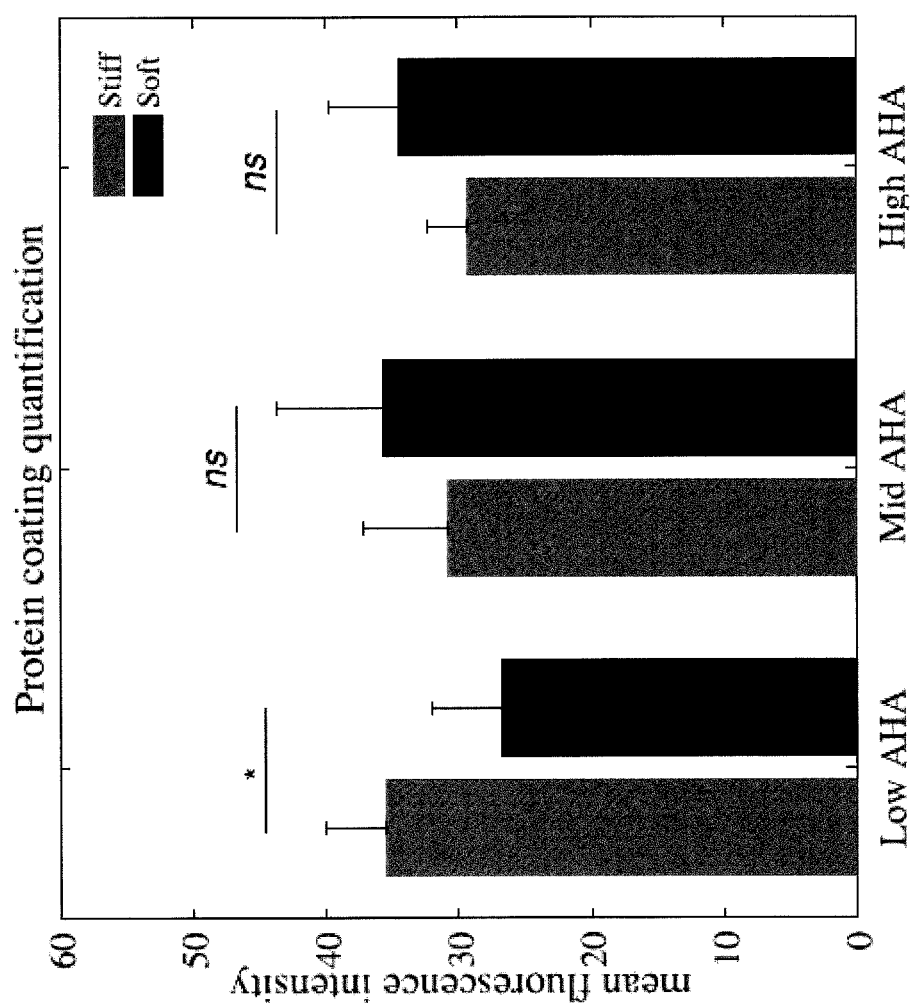
FIG. 5 shows ECM surface density as assessed by fluorescence intensity from fluorescent protein from in low AHA, mid AHA and high AHA soft and stiff gels.

Fluorescent protein was used to assess the relationship between stiffness, AHA concentration and ECM coverage. Fluorescent protein assessment of ECM surface density showed that there are no significant differences in ECM surface density between mid and high AHA soft and stiff StemBond hydrogels (FIG. 5). Thus, StemBond hydrogels facilitate a homogeneous and controllable coating of protein, independent of stiffness.

Figure 6:
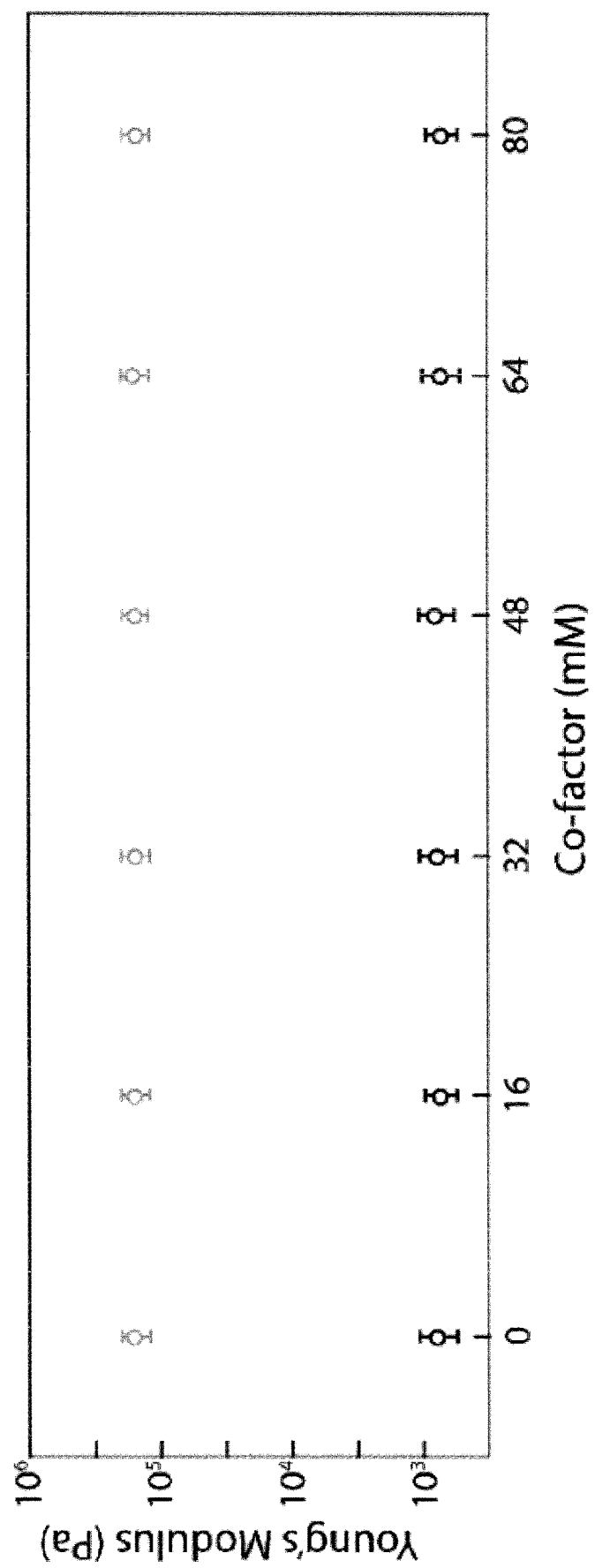
FIG. 6 shows the Youngs modulus as determined by atomic force microscopy for of StemBond hydrogels containing different concentrations of coupling compound and hence ECM ligand density.

Using atomic force microscopy, we demonstrated the ability to scale extracellular matrix tethering without affecting the stiffness of StemBond hydrogels. The Youngs modulus (Pa) was found to be unaffected by the concentration of 6AHA in StemBond hydrogels (FIG. 6). This shows that ECM ligand density can be increased without affecting stiffness and will allow highly controlled studies of mechanical signalling in which stiffness can be altered without changing the chemistry to which stem cells are exposed.

Studies were performed to demonstrate the vast potential of the hydrogels described herein. The first was an investigation of the effect of stiffness on self-renewal of naïve ES cells, and the second was the effect of stiffness on ageing in OPCs. Further studies were then performed using mouse primitive endoderm cells, human primed and naïve embryonic stem cells and human and mouse alveolar lung cells.

1. Enhancement of Naïve Self-Renewal in Embryonic Stem Cells

Figure 7:
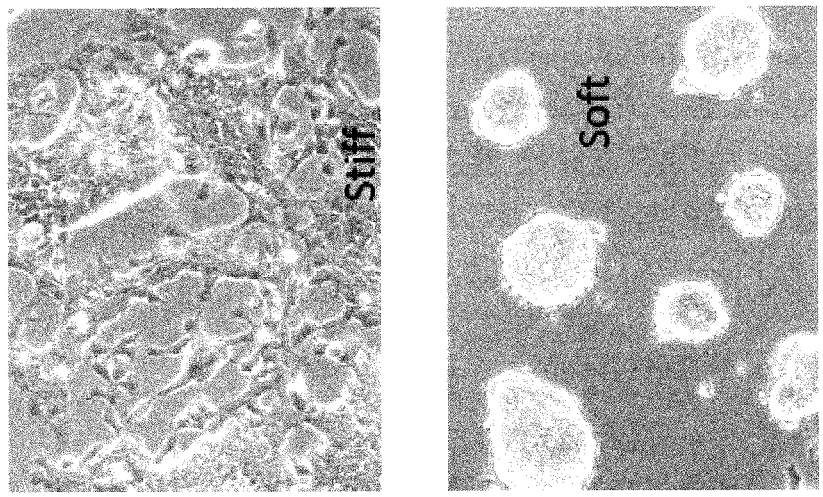
FIG. 7 shows that ES cells display spreading on stiff hydrogels that is indicative of differentiation, while they form spherical aggregates indicative of naïve pluripotency and self-renewal on soft hydrogels.

We biomimetically matched the stiffness of soft hydrogels (Soft) with that of the early mouse embryo (which we measured with atomic force microscopy to be ~0.4 kPa), and compared ES cell culture on the soft hydrogels to stiff hydrogels (Stiff, ~26 kPa) and tissue culture plastic (TCP). ES cells grown on TCP and stiff substrates spread out and formed numerous organised focal adhesions as assessed by quantification of phosphorylated Paxillin (FIG. 2E, F and FIG. 3 (top)). Significantly, mature focal adhesions are important signalling centres, known to be involved in cellular differentiation. However, we found that ES cells grown on soft substrates formed tightly aggregated spherical colonies (FIG. 2E and FIG. 7 (bottom)), highly reminiscent of their morphology in the early mouse embryo, with comparatively few organised focal adhesions (FIG. 2F and FIG. 7 (bottom)).

Figure 8:
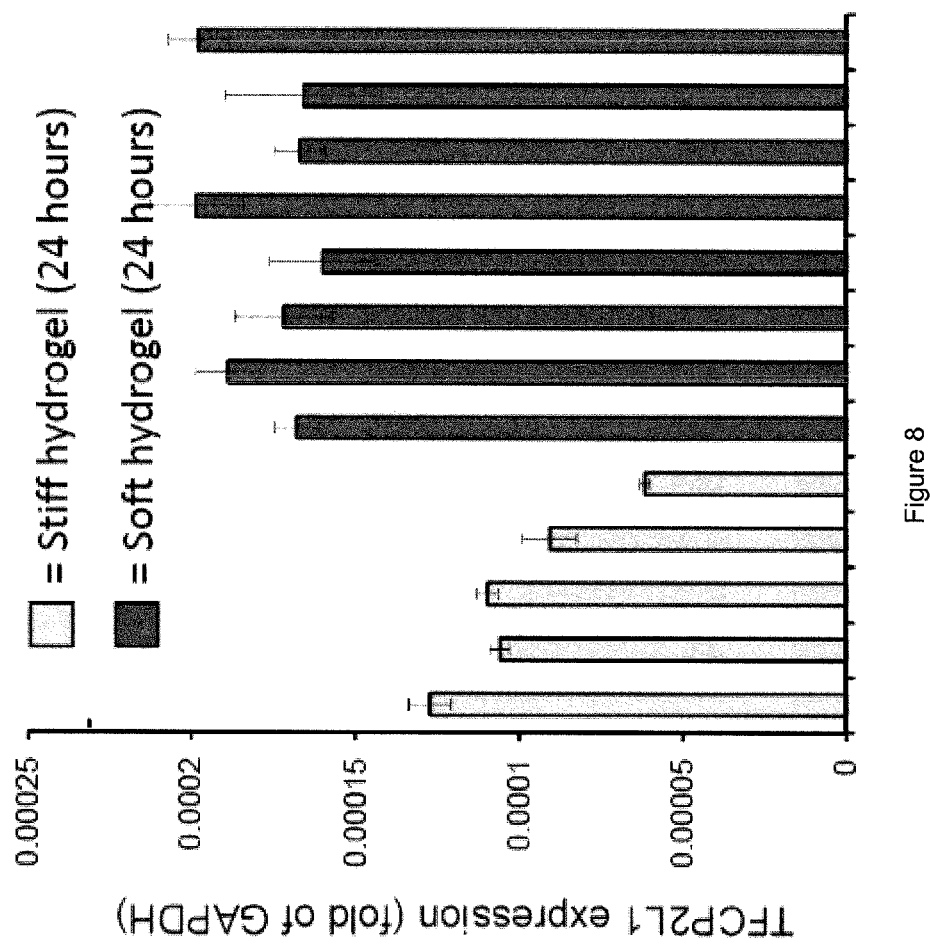
FIG. 8 shows that expression of the self-renewal factor TFCP2L1 is increased by 1.5-2× after 24 hours culture on soft hydrogels versus stiff hydrogels.
Figure 9:
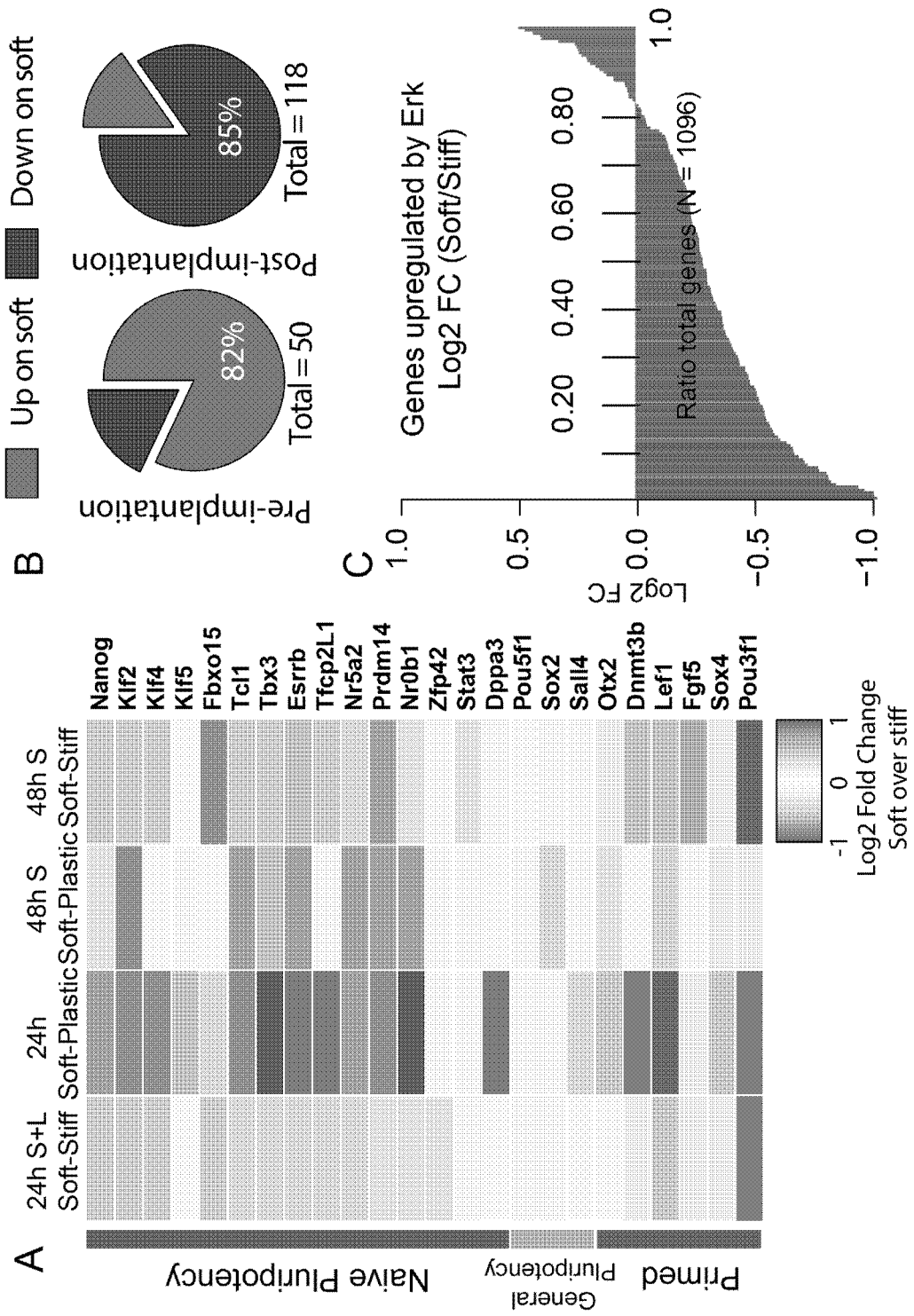
FIG. 9 shows that soft gels drive higher naïve pluripotency than stiff gels by suppressing Erk signalling. RNA sequencing was performed on ES cells in multiple conditions, including in serum+LIF (S+L) and in serum alone (S). (A) In all conditions and time points, naïve pluripotency genes are significantly upregulated on soft, and primed pluripotency genes are downregulated on soft. Colours represent Log 2 fold change of the ratio of gene expression on Soft to gene expression on Stiff. (B) Comparing to RNA sequencing data from [13], ES cells on Soft more closely resemble pre-implantation embryo, which is where naïve pluripotency is established, than post-implantation embryo, which is where primed pluripotency is established. (C) RNA sequencing was performed after removal of PD03, an Erk activity inhibitor. Genes that are activated by Erk are almost all downregulated on Soft as compared to Stiff, suggesting that Soft gels inhibit Erk activity.

To evaluate ES cell self-renewal as a function of substrate stiffness, we first performed RNA sequencing. The expression of TFCP2L1 was found to be increased in ES cells following 24 hours culture on a soft hydrogel as described herein relative to a stiff hydrogel (FIG. 8). We then tested a number of different culture conditions, including serum alone (S), serum+LIF (S+L, LIF is a cytokine that stabilises naïve pluripotency), serum+PD03 (PD03 is an inhibitor of Erk activity typically used to maintain naïve self-renewal) and serum+LIF+PD03. We showed that 'naïve genes' are all significantly upregulated in all conditions, whilst 'primed genes' [13] are significantly downregulated, on Soft compared to Stiff and TCP (FIG. 9A, which presents the results of a subset of conditions). Moreover, comparing to the RNA sequencing data from [14] which identifies genes for naïve and primed phase identity in the mouse embryo, most of the identity genes associated with naïve pluripotency in the embryo are upregulated on Soft compared to Stiff, and most of the identity genes associated with primed pluripotency in the embryo are downregulated on Soft compared to Stiff (FIG. 9B). This strongly indicates that naïve self-renewal is enhanced on Soft, whilst they simultaneously suppress primed pluripotency. Moreover, we performed an experiment on Soft and Stiff in which we removed PD03 and quantified whether Erk targets were changed as a function of substrate stiffness. Therefore, we expect the genes that immediately change are direct targets of Erk. Surprisingly, we found that over 80% of genes activated by Erk signalling are downregulated on Soft (FIG. 9C). We also found (data not shown) that over 80% of genes inhibited by Erk signalling are upregulated on Soft. This strongly suggests that Soft inhibits Erk activity. Importantly, it is known that inhibition of Erk signalling stabilises naïve pluripotency [15]; therefore, the suppression of Erk is likely the mechanism by which Soft is optimally maintaining naïve self-renewal.

Figure 10:
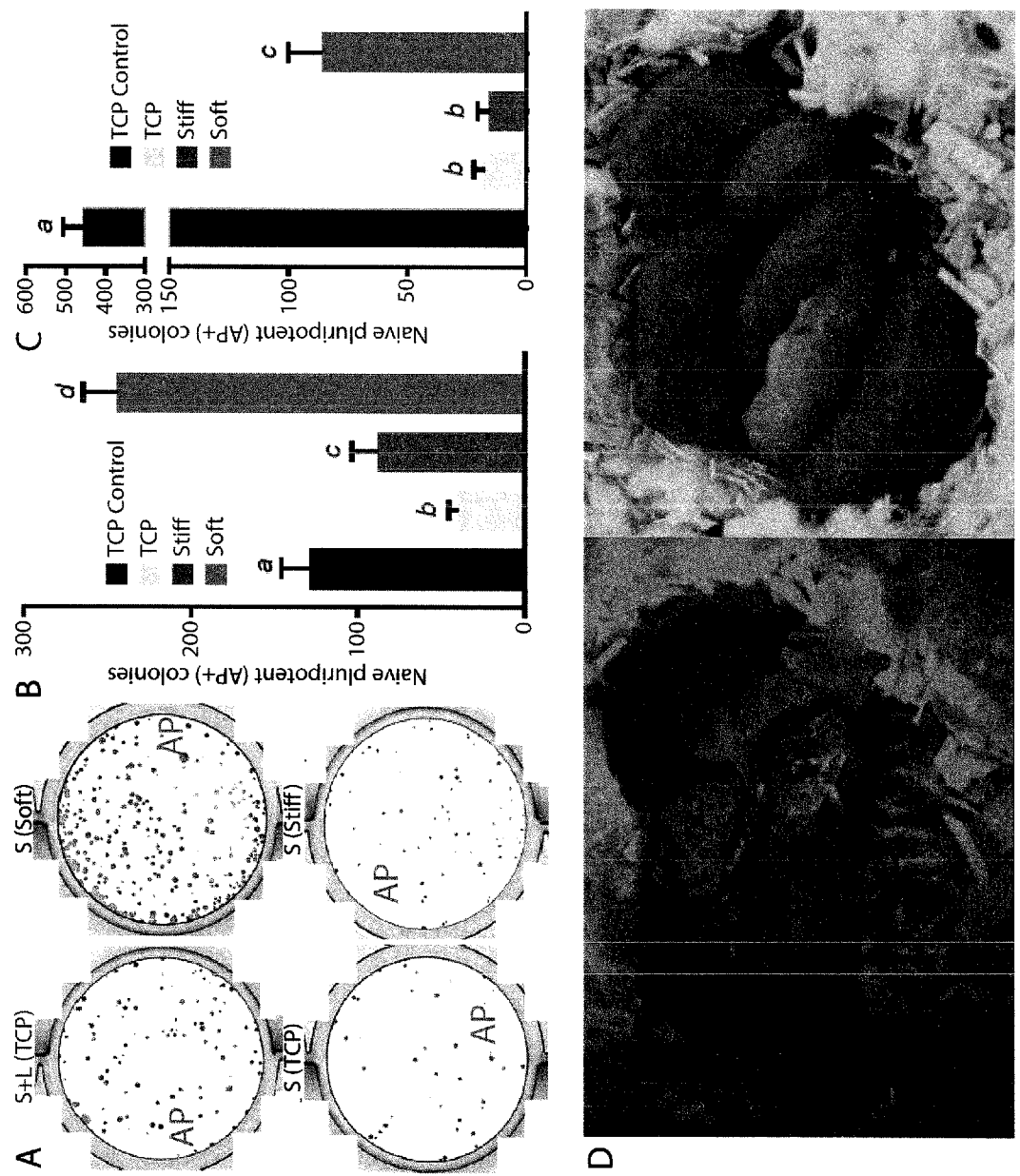
FIG. 10 shows that soft gels generate significant functional improvement in ES cells. (A) ES cells kept in either S+L or S for 5 days were replated in 2i+LIF, which only allows naïve self-renewal for cells that remained naïve at the time of replating. Naïve self-renewal is assessed by Alkaline Phosphate (AP) staining (purple). Cells cultured in S+Soft were able to form many more naïve colonies than any other condition, which is quantified in (B). For (B, C) the letters denote statistical significance (p<0.5), different letters indicate that the distributions are different in a statistically significant way. (C) ES cells were cultured in N2B27, a differentiation medium, for 3 days before replating in 2i+LIF. Again, cells maintained on Soft form many more naïve colonies than any other condition. (D) A new minimal media consisting of N2827+PD03 was then tested to see if naïve self-renewal could be maintained on Soft. This was tested by passaging ES cells 3 times in this condition and testing for the ability to make a chimaera. 5 out of the 6 mice that were born manifest significant chimerism, indicating for the first time that this minimal media can be used to maintain naïve pluripotency only on Soft.

As a functional test of the substrates, we first performed replating assays on ES cells in 2 different differentiation conditions. In the first, we cultured ES cells in S for 5 days on Soft, Stiff, and TCP (FIG. 10A). Under standard TCP conditions for this length of time, mouse ES cells differentiate. We also cultured ES cells for 5 days in S+L, which is a naïve pluripotency condition. At that time, we replated the cells into 2i+LIF, which is a medium consisting of N2B27+ PD03+Chiron (which inhibits GSK3)+LIF. 2i+LIF maintains ES cells in a homogeneous naïve state; however, differentiated cells cannot be maintained as colonies in this media. Therefore, if cells exit naïve pluripotency and are then replated into 2i+LIF, they will not form naïve, self-renewing colonies. We measured naïve colony formation with Alkaline Phosphate (AP), and found that we get many more naïve self-renewing colonies from Soft. Surprisingly, we also found that ES cells cultured in S, which is a differentiation condition, on Soft also resulted in significantly more naïve self-renewing colonies than ES cells cultured in S+L on TCP, which is a naïve pluripotency condition (FIG. 10B). The fact that ES cells can be maintained better in a known differentiation condition on Soft than they can in a known naïve pluripotency condition on TCP is a very striking result, further indicating that the Soft StemBond™ hydrogels are optimally suited for maintaining stable ES cell culture.

The second experiment is similar, but uses N2B27 alone for differentiation of cells for 3 days. Here, we see that there are comparatively few naïve self-renewing colonies that can be recovered from Stiff or TCP, but a very large number from Soft (FIG. 10C). As expected, there is some loss as compared to control, which is a passage of ES cells in 2i+LIF into 2i+LIF. Self-renewal of naïve ES cells was therefore significantly enhanced on the soft hydrogel, both molecularly and functionally. We found that adding PD03 to N2B27 without the other inhibitors appeared to allow for naïve self-renewal on Soft alone. Importantly, no one has yet used N2B27+PD03 to maintain naïve self-renewal in ES cells. We passaged ES cells in this minimal media condition on Soft for 3 passages, and were able to produce 5/6 chimeras (FIG. 10D). This indicates that we are able to use the most minimal media condition, to our knowledge, ever used to maintain naïve pluripotency.

Figure 14:
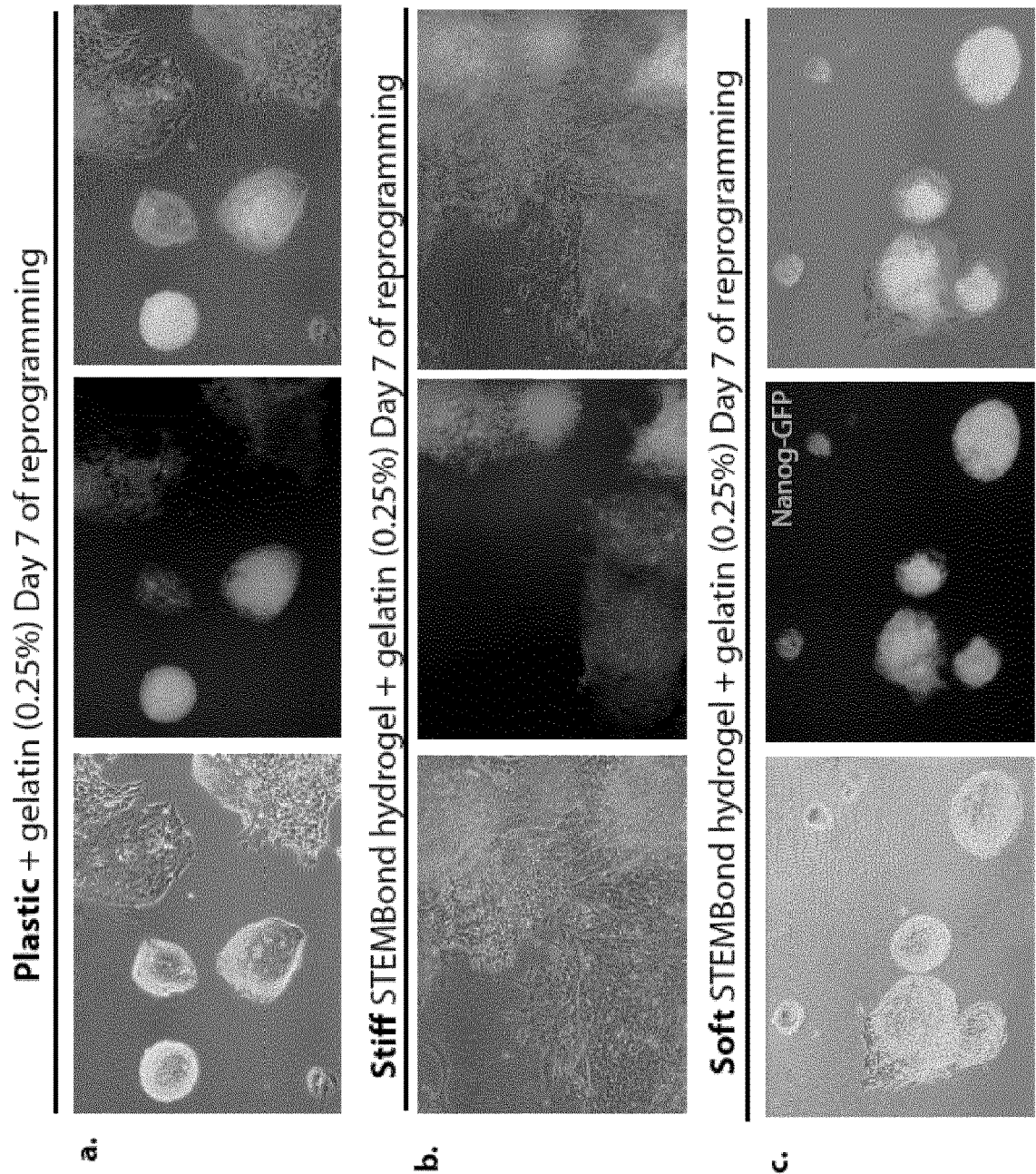
FIG. 14 shows somatic cell reprogramming on STEMBond™ hydrogels. MEF-derived Pre-iPS cells overexpressing MBD3 and Nanog (Santos, R. et al 2016, *Cell Stem Cell*, 15 (1), 102) could be successfully reprogrammed on STEMbond hydrogels. Cells expressing the Nanog-GFP reporter are successfully reprogrammed to the pluripotent state. MEF-Pre iPS were plated at equivalent density via FACS into 2i+LIF medium and either (a) plastic, (b) stiff, or (c) soft STEMBond™ gels coated with gelatin.

MEF-derived Pre-iPS cells overexpressing MBD3 and Nanog were cultured at equivalent density into 2i+LIF medium and either (a) plastic, (b) stiff, or (c) soft Stem-Bond™ gels coated with gelatin (FIG. 14). The cells were successfully successfully reprogrammed to the pluripotent state on the StemBond™ hydrogels.

Figure 15:
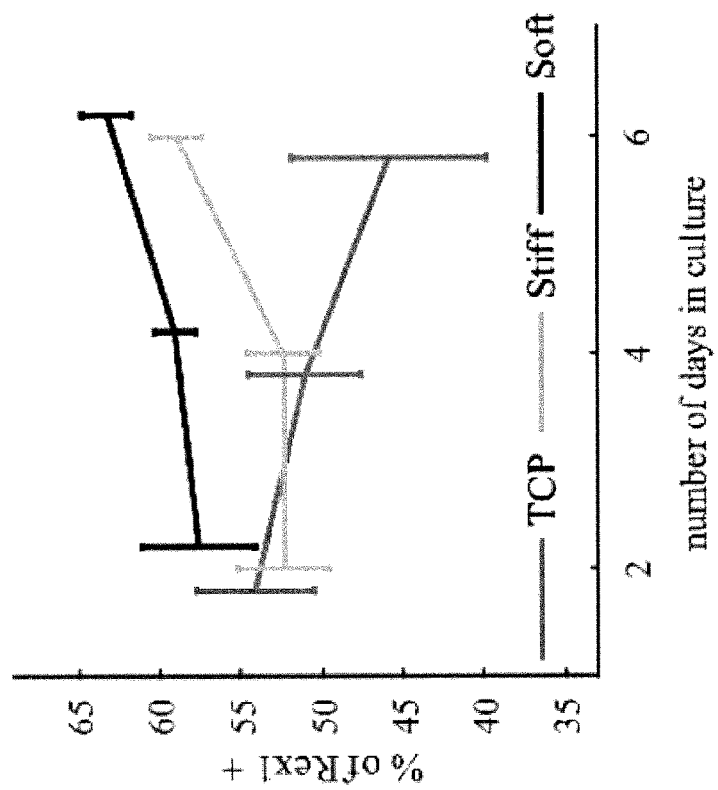
FIG. 15 shows fluorescent signal from naïve pluripotency marker Rex1:GFP and % Rex1+ cells for mouse embryonic stem cells cultured on stiff and soft StemBond hydrogels, relative to standard tissue culture plastic (TCP).
Figure 15:
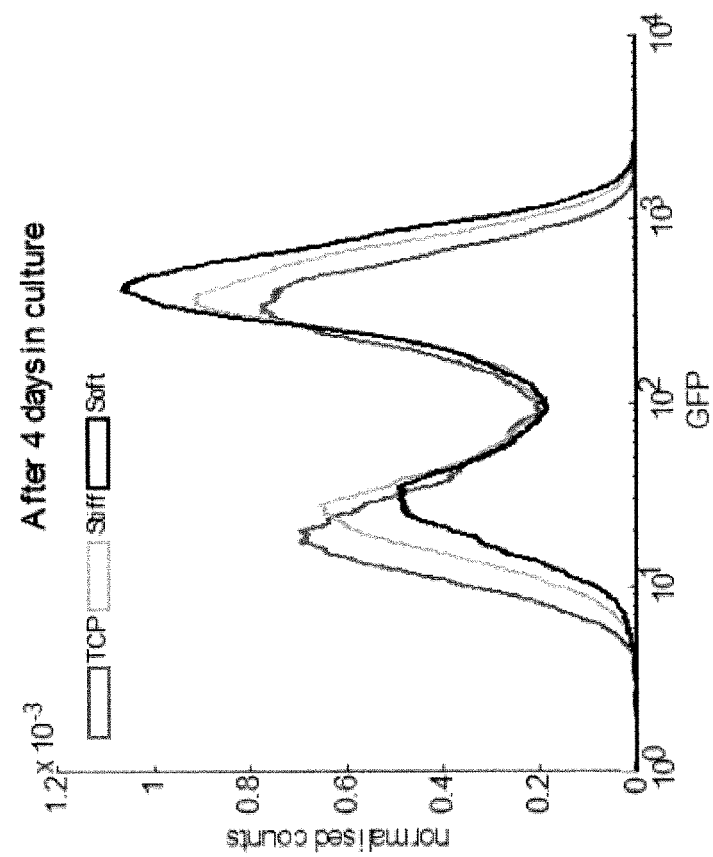

Rex1:GFP is a fluorescent marker of pluripotency in embryonic stem (ES) cells. Using the fluorescent signal from this marker, we identified how effectively the naïve, self-renewing stem cell state is maintained in culture on StemBond hydrogels. When compared to standard tissue plastic culture conditions, Rex1 levels were shown to remain significantly high over multiple passages on both stiff and soft StemBond™ hydrogels (FIG. 15). StemBond™ hydrogels were found to maintain more homogeneous cultures than standard tissue-culture plastic protocols with improved control over maintenance of pluripotency in the ES cells.

2. Reversal of Aging in Oligodendrocyte Progenitor Cells (OPCs).

OPCs are the progenitor cell population for oligodendrocytes, which are responsible for myelination of axons. Diseases such as multiple sclerosis are caused by dysfunction in the capability of oligodendrocytes to maintain axonal myelination. These diseases are exacerbated by the fact that, like many adult stem and progenitor cell populations, the function of OPCs is highly impaired with ageing. The number of OPCs does not change with age, yet aged OPCs have a marked decline in their capacity to proliferate and differentiate into myelin sheath forming oligodendrocytes. Freshly harvested neonatal rat OPCs proliferate and differentiate ~8 times the rate of freshly harvested aged rat (between 14 months and two years) OPCs.

Figure 11:
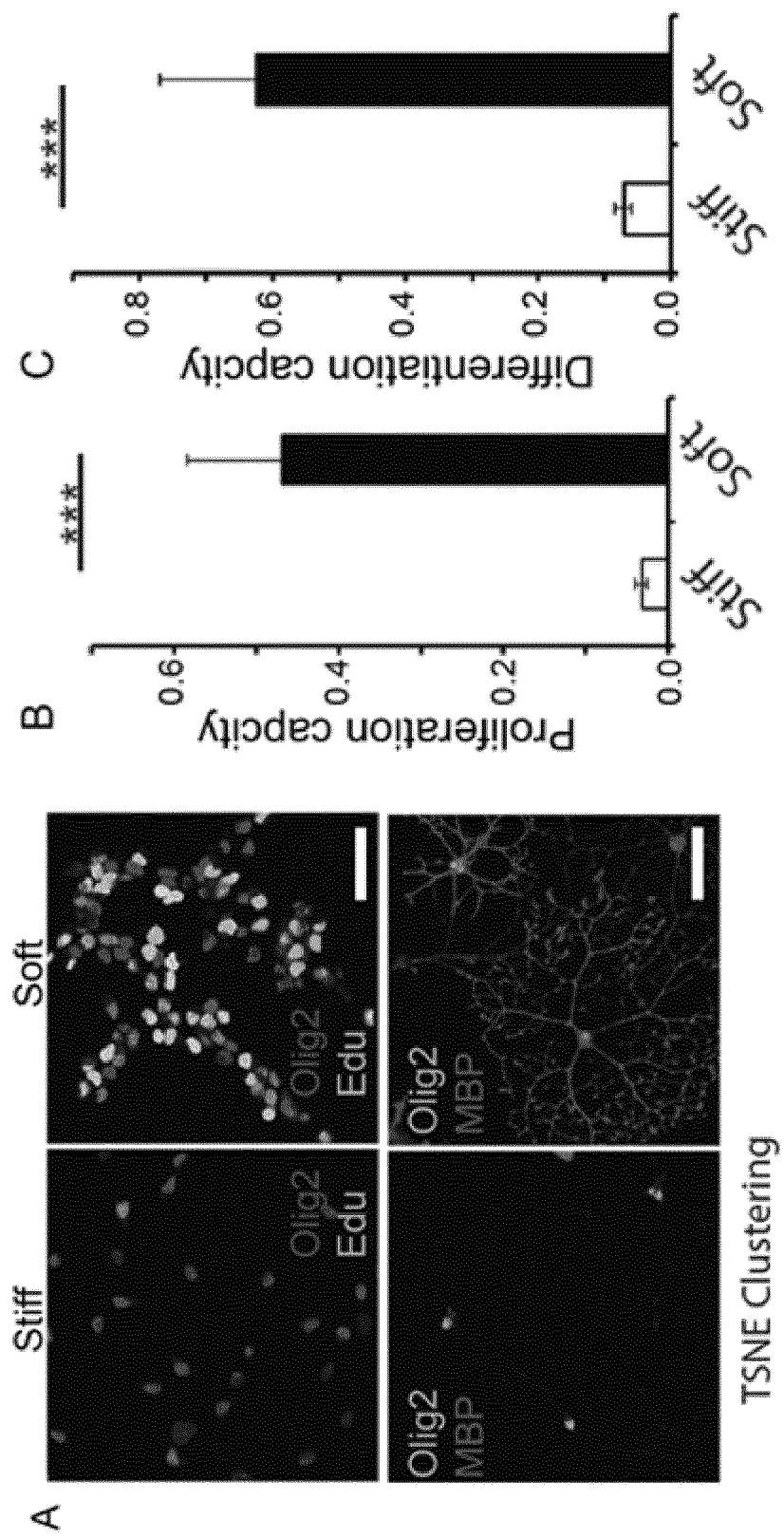
FIG. 11 shows that soft hydrogels rejuvenate aged OPCs. (A, B, C) Proliferation capacity and differentiation capacity, as measured by Edu and myelin basic protein (MBP) respectively, increase significantly on Soft as compared to Stiff. (D) RNA sequencing was performed on OPCs, and we found, looking at genome-wide data, that aged OPCs on Soft cluster with neonatal OPCs as opposed to aged OPCs. (E) Using a correlation analysis from the RNA sequencing data, OPCs on Soft cluster with neonatal OPCs, regardless of physiological age. Here dark blue means correlation of 1, and white means correlation of 0.
Figure 11:
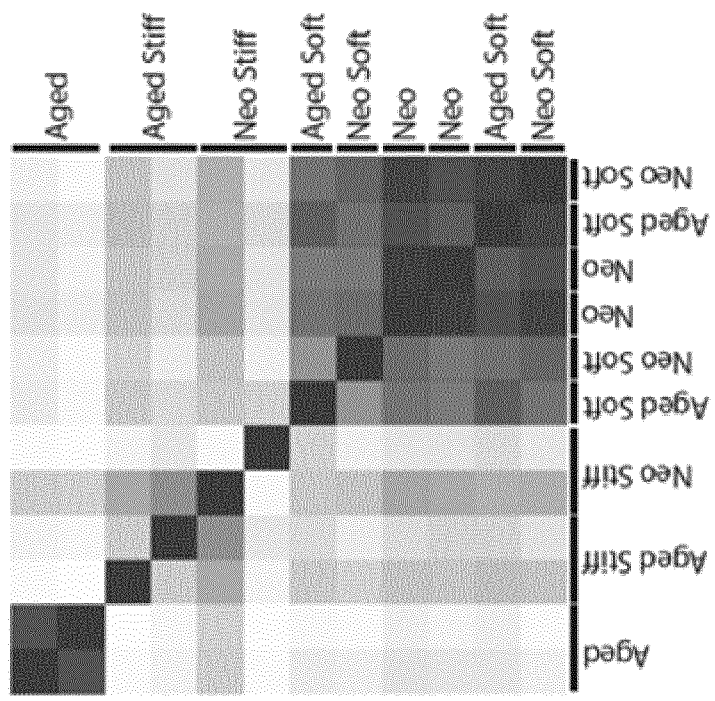
Figure 11:
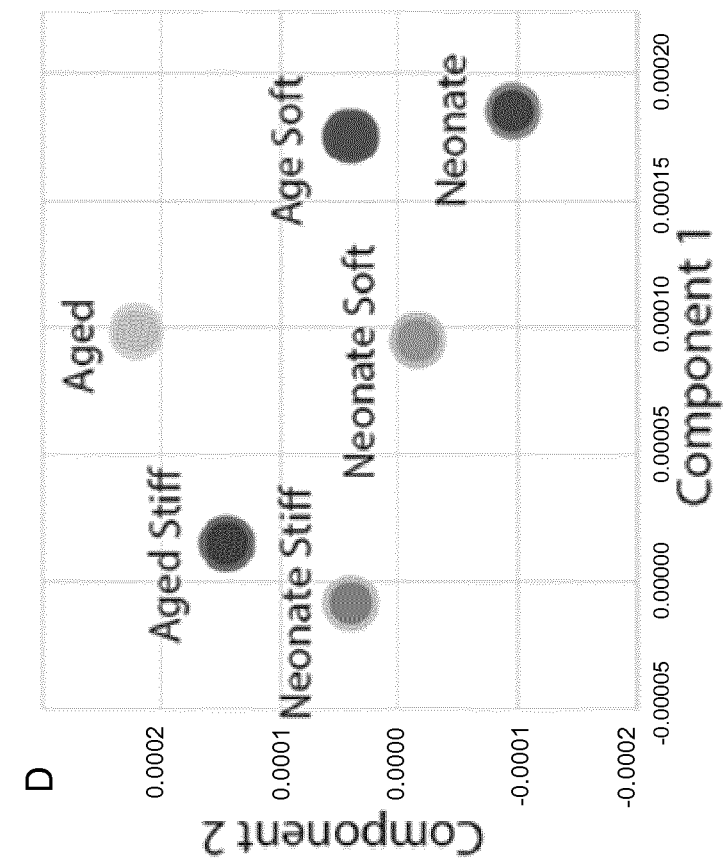
Figure 12:
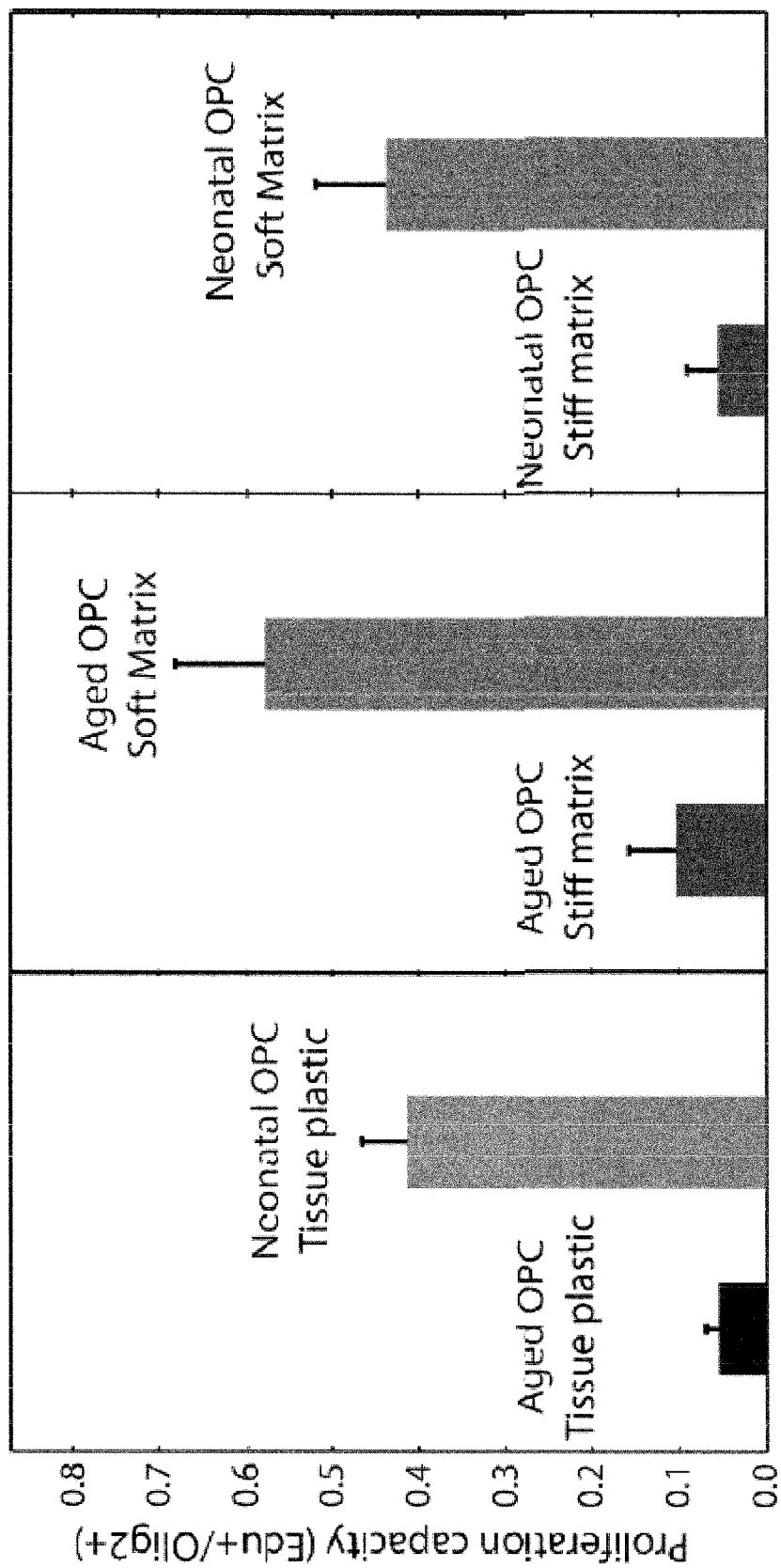
FIG. 12 shows a comparison of the proliferation capacity of aged and neonatal OPCs cultured on soft hydrogel, stiff hydrogel and TCP substrates.
Figure 13:
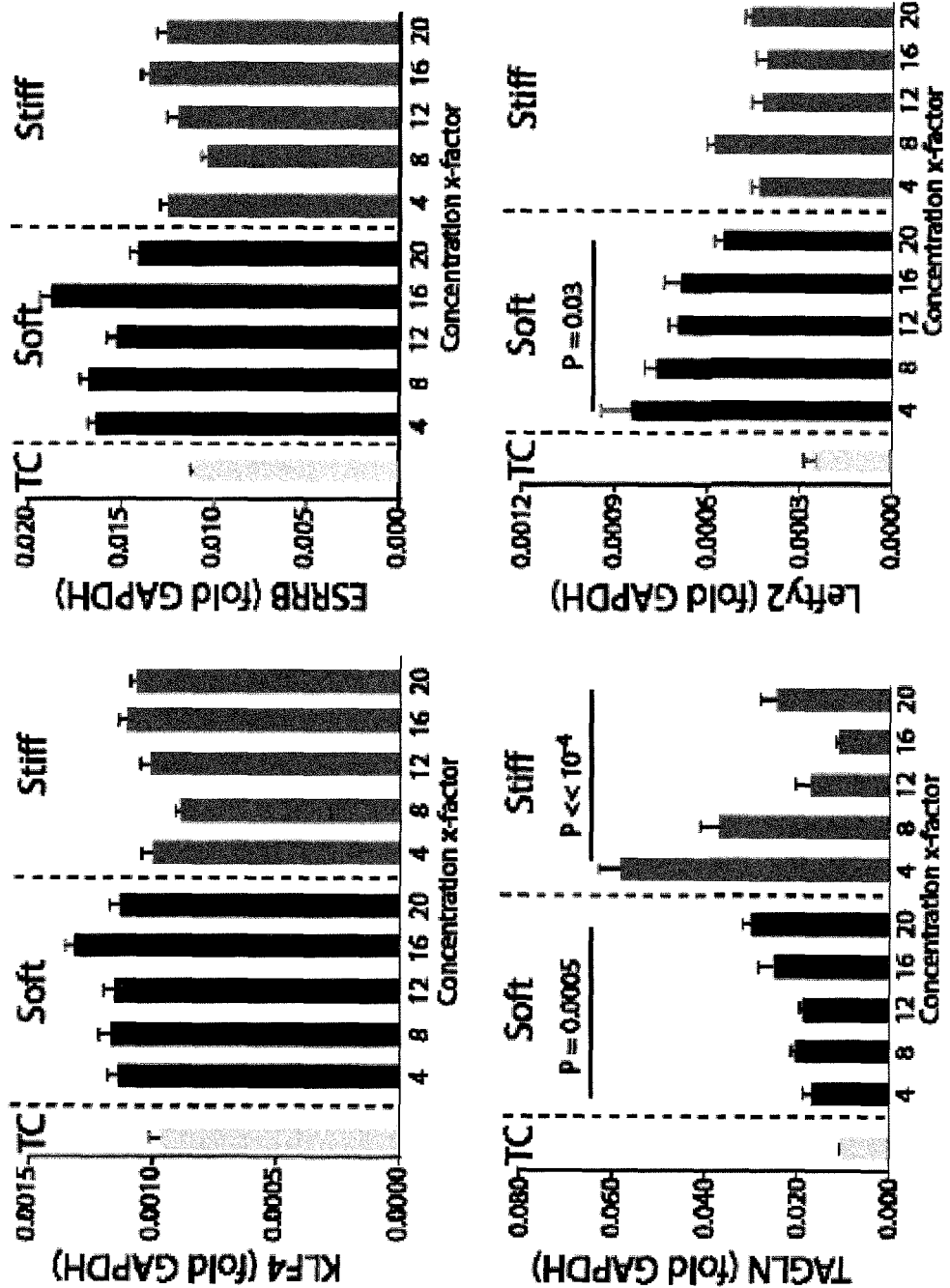
FIG. 13 shows changes in the expression of KLF4, ESRRB, TAGLN and Lefty2 for soft and stiff hydrogels containing different amounts of 6AHA.

Since progenitor cells' microenvironments are known to affect their function, we hypothesized that we could use the soft hydrogels described herein to reverse the ageing effect in OPCs. To test the effects of matrix stiffness on CNS progenitor cells, we developed synthetic polyacrylamide hydrogels functionalized with laminin that have similar stiffness to those of the softer neonatal and the stiffer aged brain. These hydrogels were designed to present the same ECM composition and density to the cells independent of stiffness. MACs sorted aged OPCs plated on the stiff, aged-brain like hydrogels showed only ~5% of cells proliferated following a 5 hour EdU pulse (FIG. 11A, B, FIG. 12). However, ~55% of aged OPCs plated on neonate-brain like hydrogels were proliferating as measured by EdU. Aged OPCs cultured on soft hydrogels therefore proliferated and differentiated ~10-fold better than aged OPCs on stiff hydrogels. As a comparison, on conventional culture substrates, the proliferation capacity of neonatal OPCs, as determined by the same experimental procedure, is ~0.45 while aged OPCs is ~0.10. When these cells were placed under differentiation conditions, more than 50% of aged OPCs on soft hydrogels differentiated into myelin basic protein (MBP) expressing oligodendrocytes whereas only ~5% of cells differentiated into myelin basic protein (MBP) expressing cells on stiff gels. Similarly, MACs sorted neonatal OPCs plated on soft and stiff hydrogels phenocopied the proliferation and differentiation rates of the aged OPCs. These data reveal that softening the environment to a more neonate-like environment improves both the proliferative and differentiation capacity of OPCs, regardless of their physiological age.

To confirm that a soft environment rejuvenates aged OPCs, we performed RNA sequencing on acutely isolated aged and neonatal OPCs, and both cell types seeded on the stiff and soft hydrogels. We found that OPCs isolated from both neonates and aged rats and cultured on soft hydrogels transcriptomically resemble freshly isolated neonatal OPCs more closely than aged OPCs and cluster with neonatal OPCs. Conversely, we found that both neonate and aged OPCs cultured on stiff hydrogels resemble aged OPCs more closely than they do neonatal OPCs or OPCs cultured in soft environments and cluster with aged OPCs. A correlation analysis revealed that, regardless of physiological age, OPCs cultured on soft hydrogels closely resemble freshly harvested neonatal OPCs (FIG. 11E). The fact that we can entirely rejuvenate aged adult progenitor cells on the soft hydrogels, is significant and shows that we can use stiffness alone to reverse ageing with soft hydrogels.

Moreover, ~20% of the most significant differentially expressed genes (p≤0.05) increased in expression in aged OPCs on soft over stiff hydrogels also were the genes enriched in neonatal over aged OPCs. Over 50% of the gene sets enriched for in aged OPCs on soft hydrogels were also enriched for in neonatal OPCs. Finally, expression of genes associated with many of these enriched gene sets such as Pdgfra, Ascl1, and Lmnb1 are also increased in expression in both neonatal OPCs and in OPCs grown on soft hydrogels. These results show both that a soft neonate-like environment can rejuvenate aged OPCs in terms of network-wide gene expression and can reinstate transcriptional programs associated with the reversal of the aging process.

3. Mouse Primitive Endoderm Culture

Primitive Endoderm (PrE) is one of three cell lineages of the early blastocyst which makes the yolk sac of the embryo. It's an essential lineage in embryonic development. Of the three lineages, two are able to be maintained in culture as an accurate analogue of their in vivo phenotype. PrE cells, however, are transformed to a migratory cell type in culture and are no longer comparable to their in vivo counterpart. In order to achieve the goal of building synthetic embryos with all extraembryonic lineages, al three blastocyst cell lineages must be maintained in culture in a self-renewing state.

Figure 16:
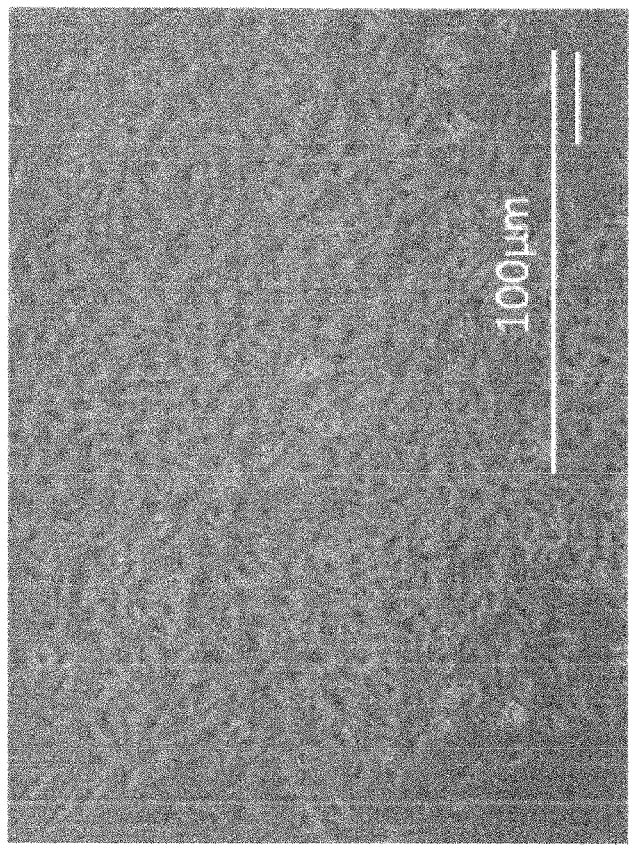
FIG. 16 shows mouse primitive endoderm cells cultured on StemBond hydrogel and standard tissue culture plastic (TCP)
Figure 16:
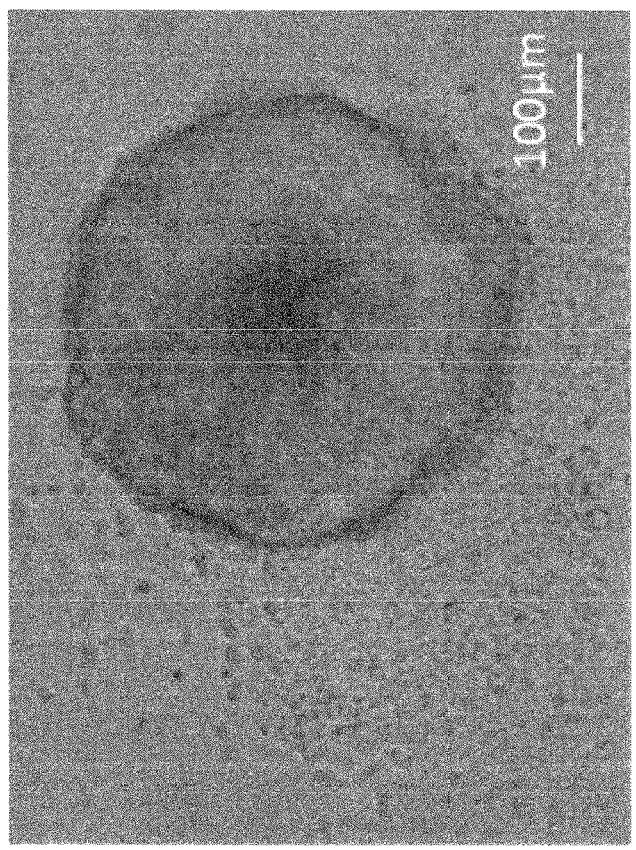
Figure 17:
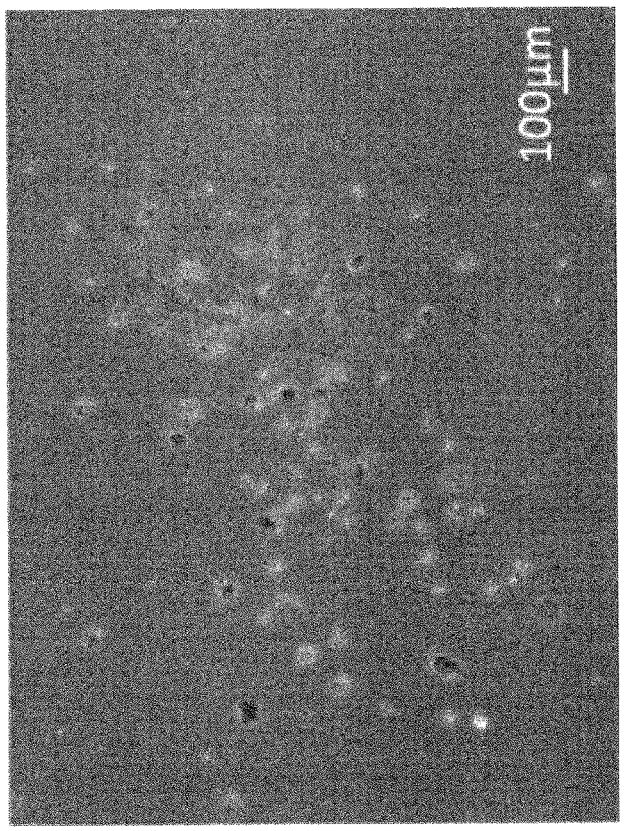
FIG. 17 shows mouse primitive endoderm cells cultured on StemBond hydrogel then passaged back to either StemBond hydrogel or standard tissue culture plastic (TCP)
Figure 17:
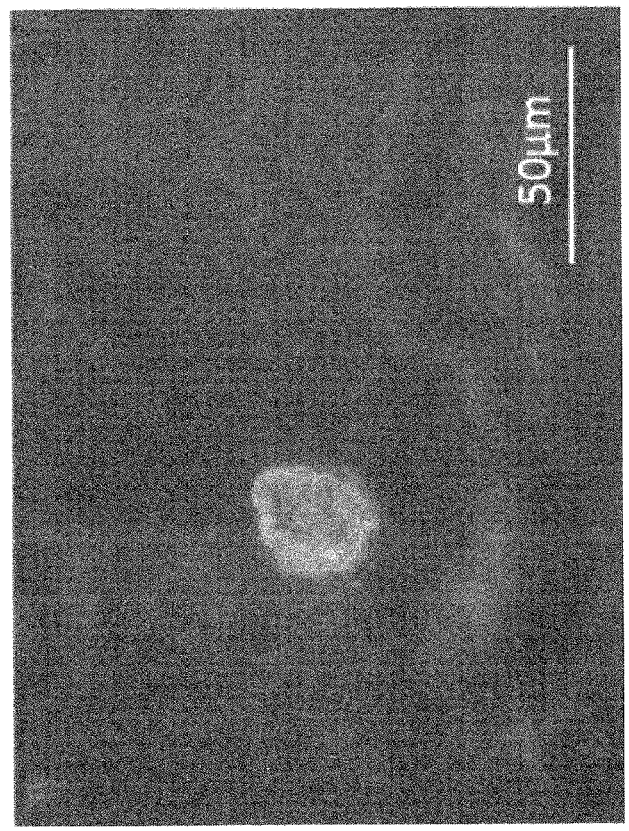

We cultured primitive endoderm (PrE) cells on StemBond™ hydrogels and maintained a self-renewing PrE phenotype in culture for the first time. On StemBond™, the PrE cells were observed to form colonies whereas the PrE cells developed altered phenotypes on tissue culture plastic (TCP) (FIG. 16). PrE colonies formed on the StemBond hydrogel were successfully passaged across StemBond gels for multiple passages. In contrast, PrE cells cultured on StemBond™ and then passaged to standard tissue culture plastic coated with fibronectin revert to the migratory cell phenotype associated with in vitro PrE culture, are unable to form colonies and/or fall to proliferate (FIG. 17).

4. Human Primed Embryonic Stem Cells

Primed embryonic stem cells have the capacity to differentiate into any somatic cell line, however are cued for differentiation into a specific lineage. This developmental stage represents the post-implantation epiblast of the human embryo. Primed hESCs are the commonly cultured on substrates such as Matrigel or Geltrex, both of which are not dearly defined nor GMP.

Figure 18:
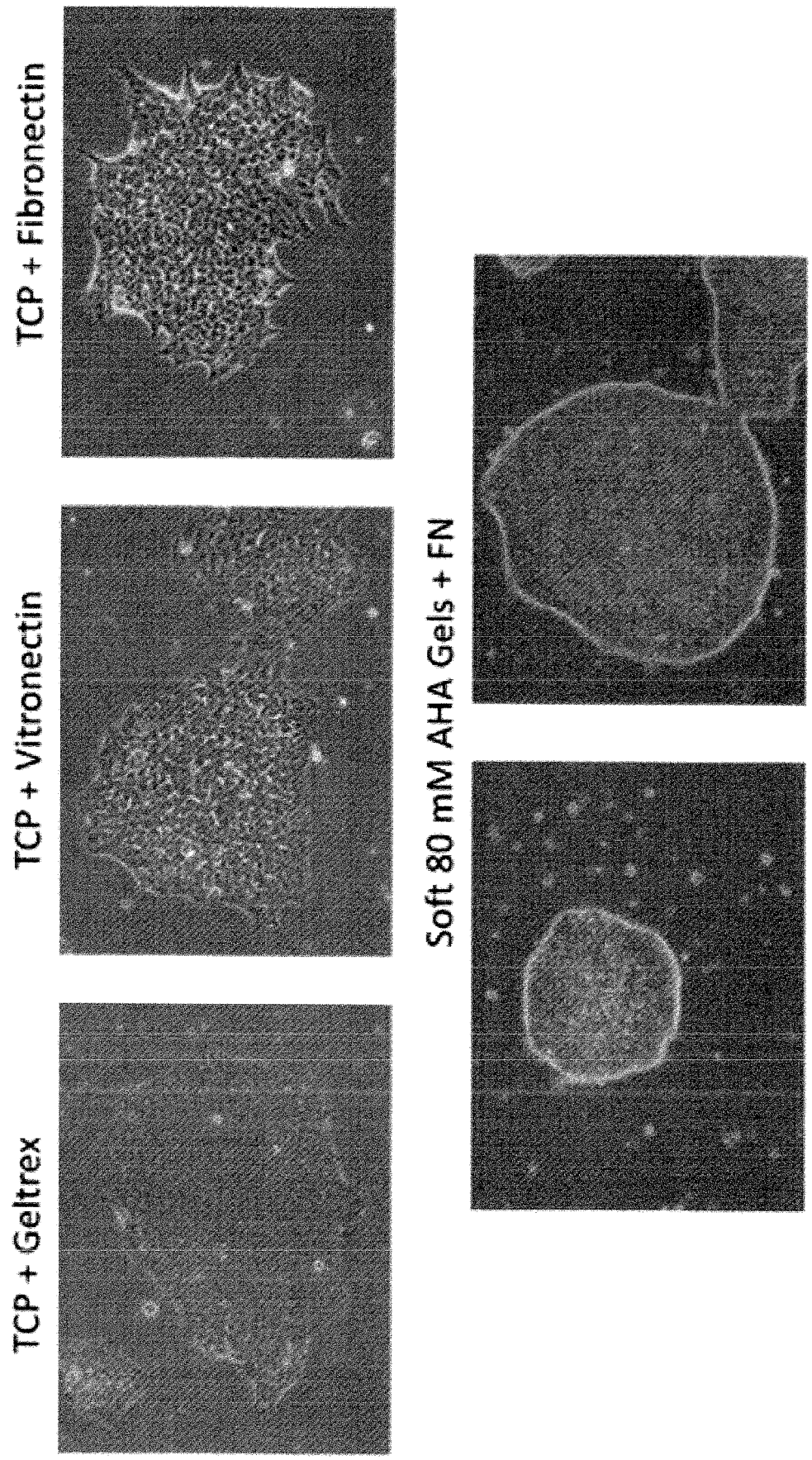
FIG. 18 shows primed hESCs cultured on soft StemBond hydrogels coated with fibronectin and tissue culture plastic coated with Geltrex, vitronectin or fibronectin

We have been successful in culturing primed hESCs on soft StemBond™ hydrogels coated with fibronectin. Cells in this culture displayed dearly improved morphology and colony forming capacity (i.e. rounder colonies with well-defined borders) when compared with tissue culture plastic coated with Geltrex, vitronectin or fibronectin (FIG. 18).

5. Human Naïve Embryonic Stem Cells

Naïve embryonic stem cells (HNES) are derived from the pre-implantation embryo, representing a blank canvas of developmental potential. Each HNES cell has the unbiased capacity to differentiate towards any cell type. Controlling and guiding this potential is a key element of stem cell research and forms the basis of regenerative medicine.

Figure 19:
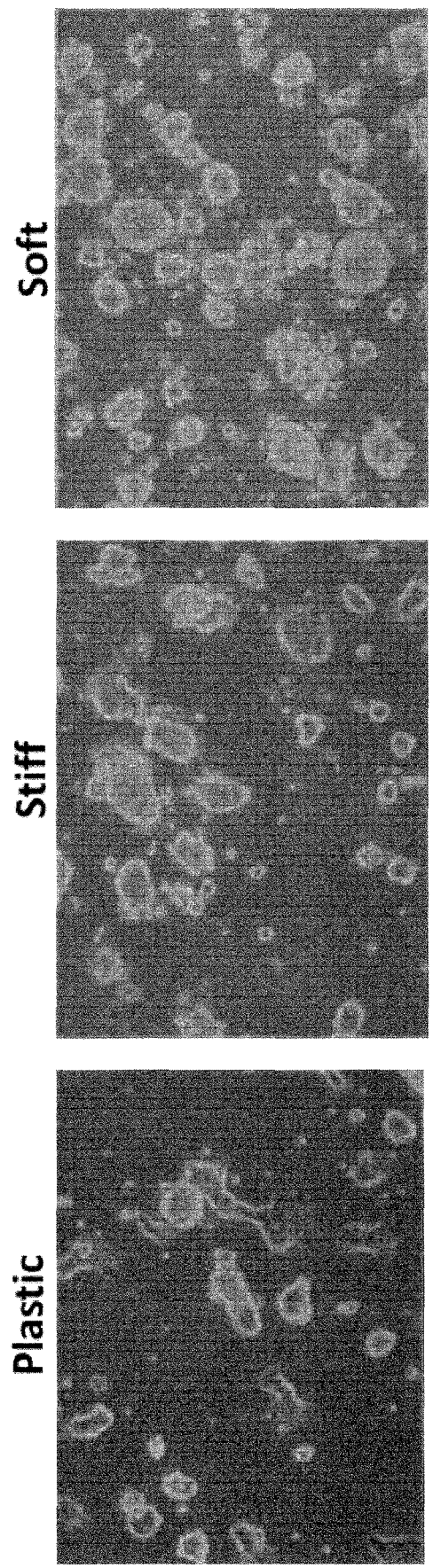
FIG. 19 shows naïve hESCs cultured on stiff and soft StemBond hydrogels coated with laminin and tissue culture plastic coated with laminin.

StemBond™ hydrogels were used in the culture of two human naïve embryonic cell lines: HNES1 and cR-H9 for 4 days. Each line displayed improved morphology and colony forming efficiency using laminin coated stiff and soft StemBond hydrogels when compared with laminin coated tissue plastic (FIG. 19).

6. Human and Mouse Alveolar Luna Cells

Figure 20:
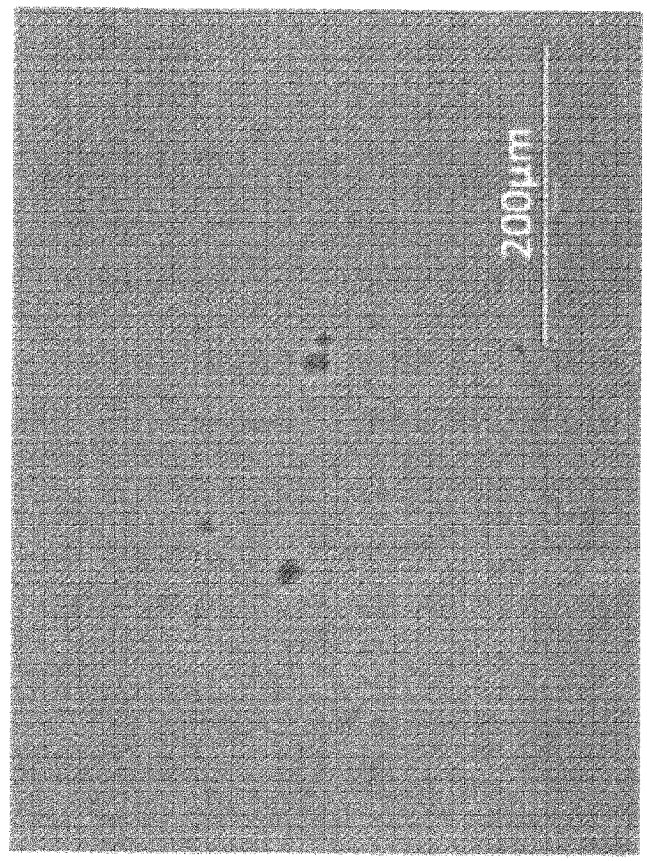
FIG. 20 shows human and mouse alveolar lung cells cultured on Matrigel and soft StemBond hydrogel coated with fibronectin.
Figure 20:
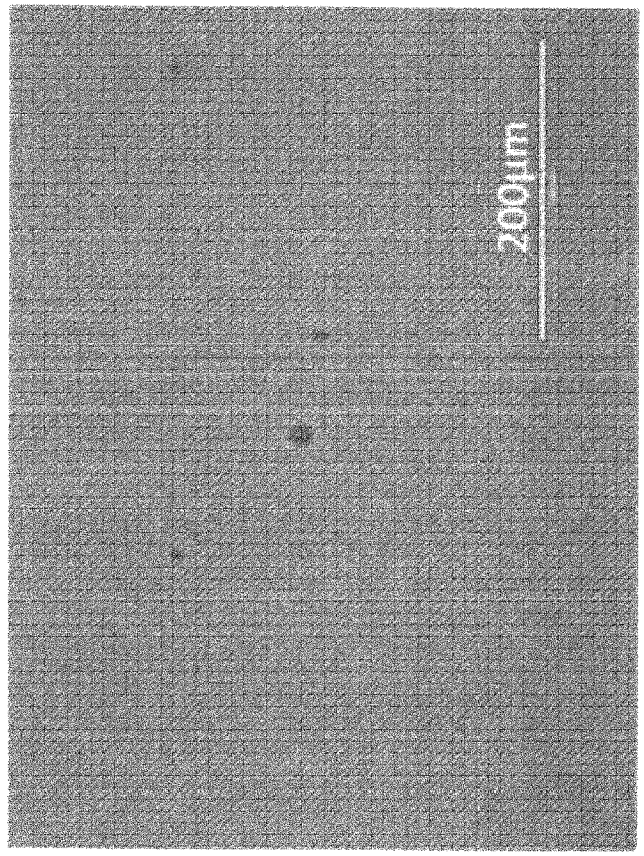

Human and Mouse Alveolar Lung Cells are cultured as standard on Matrigel. Matrigel is a commonly used, however ill-defined substrate which cannot conform to GMP standards. 3 days post seeding, soft StemBond™ hydrogel supports mouse alveolar lung cell adhesion and growth. For at least the first 5 days of culture, StemBond with a fibronectin coating was found to be effective a culture condition as the Matrigel alternative (FIG. 20).

We have shown that the PA-8AHA co-polymer hydrogels described herein can be used to independently control stiffness and ECM density and composition. With these, we developed a soft, highly adhesive hydrogel optimised for stem cells from the early embryo and from the central nervous, which are both soft tissues. Our soft hydrogel was optimal for maintaining stable, naïve self-renewal in ES cells, and can be used to develop new, minimal media conditions for naïve pluripotency. We also used the soft hydrogel to reverse ageing in a progenitor cell population from the central nervous system. The PA-6AHA co-polymer hydrogels described herein can be easily adapted into any modality and scaled up. They can be straightforwardly translated into any laboratory or clinical setting and may be useful in maintaining stem cell cultures for regenerative medicine.

REFERENCES

1. Meilhac, S. M., et al., *Active cell movements coupled to positional induction are involved in lineage segregation in the mouse blastocyst*. Developmental biology, 2009. 331(2): p. 210-21.
2. Wang, N., J. D. Tytell, and D. E. Ingber, *Mechanotransduction at a distance: mechanically coupling the extracellular matrix with the nucleus*. Nature reviews. Molecular cell biology, 2009. 10(1): p. 75-82.
3. Geiger, B., J. P. Spatz, and A. D. Bershadsky, *Environmental sensing through focal adhesions*. Nature reviews. Molecular cell biology, 2009. 10(1): p. 21-33.
4. Connelly, J. T., et al., *Actin and serum response factor transduce physical cues from the microenvironment to regulate epidermal stem cell fate decisions*. Nat Cell Biol, 2010.12(7): p. 711-8.
5. Engler, A. J., et al., *Matrix elasticity directs stem cell lineage specification*. Cell, 2006. 126(4): p. 677-89.
6. Versaevel, M., T. Grevesse, and S. Gabriele, *Spatial coordination between cell and nuclear shape within micropatterned endothelial cells*. Nat Commun, 2012. 3: p. 671.
7. Huebsch, N., et al., *Harnessing traction-mediated manipulation of the cell/matrix interface to control stem-cell fate*. Nat Mater, 2010. 9(6): p. 518-26.
8. Gerecht, S., et al., *Hyaluronic acid hydrogel for controlled self-renewal and differentiation of human embryonic stem cells*. Proc Natl Acad Sci USA, 2007. 104(27): p. 11298-303.

9. Caiazzo, M., et al., *Defined three-dimensional microenvironments boost induction of pluripotency*. Nat Mater, 2016.15(3): p. 344-52.
10. Park, J. S., et al., *The effect of matrix stiffness on the differentiation of mesenchymal stem cells in response to TGF-beta*. Biomaterials, 2011.32(16): p. 3921-30.
11. Guilak, F., et al., *Control of stem cell fate by physical interactions with the extracellular matrix*. Cell Stem Cell, 2009.5(1): p. 17-26.
12. Trappmann, B., et al., *Extracellular-matrix tethering regulates stem-cell fate*. Nat Mater, 2012. 11(7): p. 642-9.
13. Nichols, J. and A. Smith, *Naive and primed pluripotent states*. Cell Stem Cell, 2009.4(6): p. 487-92.
14. Borovlak, T., et al., *Lineage-Specific Profiling Delineates the Emergence and Progression of Naive Pluripotency in Mammalian Embryogenesis*. Dev Cell, 2015. 35(3): p. 366-82.
15. Nichols, J., et al., *Suppression of Erk signalling promotes ground state pluripotency in the mouse embryo*. Development, 2009.136(19): p. 3215-22.

The invention claimed is:
1. A substrate for culture of mammalian stem and progenitor cells culture comprising;
   (i) a co-polymer hydrogel formed from a co-polymer, wherein the co-polymer comprises cross-linked chains of monomeric units of acrylamide, a N,N' methylenebisacrylamide (bisacrylamide) cross-linking agent, and a coupling compound in the hydrogel; and
   (ii) a cell adhesion molecule, said cell adhesion molecule being covalently coupled to coupling compound monomeric units of the co-polymer,
   wherein the coupling compound is 6-acrylamidohexanoic acid (6AHA) and
   the co-polymer hydrogel comprises 1-10% (w/v in g/100 ml) acrylamide monomeric units and 10 to 100 mM 6AHA,
   wherein the substrate constitutes a stable tunable synthetic stem cell niche for maintenance of stable mammalian stem and progenitor cell cultures;
   wherein concentration of the monomeric units of acrylamide in the co-polymer hydrogel controls stiffness of the substrate; and
   wherein stiffness of the hydrogel corresponds to stiffness of a biological tissue;
   wherein the cell adhesion molecule forms a molecular anchoring site for the cultured mammalian stem or progenitor cells;
   wherein concentration of the coupling compound in the copolymer hydrogel controls cell adhesion molecule density of the substrate; and
   wherein density of the cell adhesion molecule reflects density of the cell adhesion molecule in a biological tissue;
   wherein stiffness of the substrate and density of the cell adhesion molecules are independently tunable;
   wherein the substrate with a defined stiffness enables selection of cells from specific tissues; and
   wherein the substrate with a high density of cell adhesion molecules enables selection of mammalian stem or progenitor cells that originate from a high adhesion environment; and the substrate with a low density of cell adhesion molecules enables selection of mammalian stem or progenitor cells that originate from a low adhesion environment.

2. The substrate according to claim 1 wherein
   wherein stiffness of the hydrogel substrate reflects the stiffness of a hard tissue; the stiffness of an intermediate tissue; or the stiffness of a soft tissue;
   wherein stiffness of the hard tissue is from 50 kPa to 10-kPa, inclusive;
   wherein stiffness of the intermediate tissue is from 5 kPa to 30 kPa, inclusive; and
   wherein stiffness of the soft tissue is from 0.1 kPa to 1.2 kPa inclusive.

3. The substrate according to claim 1 wherein the cell adhesion molecule comprises a primary amine group.

4. The substrate according to claim 1 wherein the cell adhesion molecule is an integrin ligand.

5. The substrate according to claim 1 wherein the cell adhesion molecule is fibronectin.

6. The substrate according to claim 1 wherein the cell adhesion molecule is laminin.

7. A mammalian cell culture system comprising:
   (a) a substrate according to claim 1; and
   (b) a cell culture medium.

8. The mammalian cell culture system according to claim 7 wherein the mammalian stem cells include stem cells selected from the group consisting of corneal (limbal) stem cells; embryonic stem cells; mesenchymal stem cells, adipose-derived stem cells, endothelial stem cells, dental pulp stem cells, skin epidermal stem cells; gut (intestinal) stem cells; orogenital stem cells; bronchial and other epithelial stem cells; muscle cells, haematopoietic stem cells, amniotic stem cells bone marrow stromal stem cells; growth plate stem cells, iPSCs; mouse primitive endoderm (PrE) cells, and human alveolar lung cells and the mammalian progenitor cells include oligodendrocyte progenitor cells.

9. A method of culturing mammalian cells comprising;
   providing a substrate according to claim 1;
   immersing the substrate in a cell culture medium;
   seeding the substrate with mammalian stem or progenitor cells; and
   culturing the mammalian stem or progenitor cells on the substrate.

10. A method of producing a cell culture substrate comprising in order:
    producing a solution of acrylamide, bisacrylamide and coupling compound monomeric units,
    then polymerizing said monomers to form a co-polymer hydrogel comprising acrylamide and coupling compound monomeric units in the hydrogel; and
    then covalently coupling a cell adhesion molecule to the coupling compound monomeric units in the hydrogel to produce the cell culture substrate,
    wherein the coupling compound is 6-acrylamidohexanoic acid (6AHA), and
    wherein the co-polymer hydrogel comprises 1-10% (w/v in g/100 ml) acrylamide monomeric units and 10 to 100 mM 6AHA.

11. The method according to claim 10 wherein the substrate is a substrate according to claim 1.

12. The method according to claim 10 wherein the cell adhesion molecule is covalently coupled to the coupling compound monomeric units of the co-polymer hydrogel by a method comprising;
    activating the carboxyl groups of the coupling compound monomeric units with one or more activating agents, and
    reacting the activated carboxyl groups with a primary amine group of the cell adhesion molecule to form a covalent linkage.

13. The method according to claim 12 wherein the activating agents are N-(3-Dimethylaminopropyl)-N'-ethylcarbodiimide hydrochloride (EDAC) and N-hydroxysuccinimide (NHS).

14. The substrate according to claim 1 wherein the substrate is produced by a method comprising:
providing a solution of acrylamide, bisacrylamide and 6AHA monomeric units;
polymerizing said monomers to form the co-polymer hydrogel comprising acrylamide and 6AHA monomeric units; and
covalently coupling the cell adhesion molecule to the 6AHA monomeric units.

15. The substrate according to claim 1, wherein the stem cell niche is permissive for providing stem cell mechanosensing cues comprising substrate stiffness to which the stem cells of the niche respond with biochemical signaling.

16. The substrate according to claim 2, wherein the hard tissue is selected from the group consisting of osteogenic and cartilage tissue progenitor cells, osteoblasts, osteoclasts and chondrocytes.

17. The substrate according to claim 2, wherein the intermediate tissue is selected from the group consisting of myocytes, fibroblasts, differentiated mesenchymal cells, precursors and progenitors thereof.

18. The substrate according to claim 2, wherein the soft tissue is selected from the group consisting of embryonic stem cells, oligodendrocyte progenitor cells (OPCs), mouse PrE cells, human primed embryonic stem cells; human naïve embryonic stem cells; human alveolar lung cells and human alveolar lung cells.

* * * * *